US009309256B2

(12) United States Patent
Singh

(10) Patent No.: US 9,309,256 B2
(45) Date of Patent: Apr. 12, 2016

(54) PHARMACEUTICALLY ACTIVE DIMERS LINKED THROUGH PHENOLIC HYDROXYL GROUPS

(71) Applicant: OrphoMed LLC, Mill Valley, CA (US)

(72) Inventor: Nikhilesh Nihala Singh, Mill Valley, CA (US)

(73) Assignee: OrphoMed, Inc., Mill Valley, CA (US)

( * ) Notice: Subject to any disclaimer, the term of this patent is extended or adjusted under 35 U.S.C. 154(b) by 0 days.

(21) Appl. No.: 14/697,155

(22) Filed: Apr. 27, 2015

(65) Prior Publication Data
US 2015/0307505 A1 Oct. 29, 2015

Related U.S. Application Data

(60) Provisional application No. 61/985,207, filed on Apr. 28, 2014, provisional application No. 62/101,768, filed on Jan. 9, 2015, provisional application No. 62/176,883, filed on Jan. 9, 2015.

(51) Int. Cl.
| C07D 489/08 | (2006.01) |
| C07C 211/09 | (2006.01) |
| C07D 489/02 | (2006.01) |
| C07C 217/64 | (2006.01) |
| C07C 217/70 | (2006.01) |
| C07C 233/43 | (2006.01) |
| A61K 31/137 | (2006.01) |
| A61K 31/167 | (2006.01) |
| A61K 31/485 | (2006.01) |
| C07C 233/16 | (2006.01) |
| C07D 489/00 | (2006.01) |

(52) U.S. Cl.
CPC ............ *C07D 489/02* (2013.01); *A61K 31/137* (2013.01); *A61K 31/167* (2013.01); *A61K 31/485* (2013.01); *C07C 217/64* (2013.01); *C07C 217/70* (2013.01); *C07C 233/16* (2013.01); *C07C 233/43* (2013.01); *C07D 489/00* (2013.01); *C07D 489/08* (2013.01)

(58) Field of Classification Search
USPC ...................................... 546/39, 45; 564/336
See application file for complete search history.

(56) References Cited

U.S. PATENT DOCUMENTS

| 3,896,235 | A | * | 7/1975 | Harfenist | ....................... 514/616 |
| 7,056,500 | B2 | | 6/2006 | Bentley et al. | |
| 7,084,150 | B2 | | 8/2006 | Boer et al. | |
| 7,759,358 | B2 | * | 7/2010 | Crooks et al. | ................. 514/282 |
| 8,063,059 | B2 | | 11/2011 | Hermann | |
| 8,183,376 | B2 | | 5/2012 | Cheng et al. | |
| 8,461,171 | B2 | | 6/2013 | Holaday et al. | |
| 8,617,530 | B2 | | 12/2013 | Roberts et al. | |
| 8,962,647 | B1 | | 2/2015 | Guo et al. | |
| 2005/0075361 | A1 | | 4/2005 | Wang | |
| 2010/0068786 | A1 | | 3/2010 | Chmielewski et al. | |
| 2011/0160239 | A1 | | 6/2011 | Brodbeck et al. | |
| 2011/0245287 | A1 | | 10/2011 | Holaday et al. | |
| 2015/0307504 | A1 | | 10/2015 | Singh | |

FOREIGN PATENT DOCUMENTS

| EP | 1 422 230 A1 | 5/2004 |
| WO | 03/032990 A2 | 4/2003 |
| WO | 2004/103317 A2 | 12/2004 |
| WO | 2013/123824 A1 | 8/2013 |
| WO | 2015/168014 A1 | 11/2015 |
| WO | 2015/168031 A1 | 11/2015 |

OTHER PUBLICATIONS

International Search Report and Written Opinion corresponding to PCT/US2015/027820 mailed Jul. 3, 2015 (14 pages).
International Search Report and Written Opinion corresponding to PCT/US2015/027781 mailed Sep. 9, 2015 (19 pages).
Bagnol, D. et al., "Cellular Localization and Distribution of the Cloned Mu and Kappa Opioid Receptors in Rat Gastrointestinal Tract," *Neuroscience* (Nov. 1, 1997); 81(2):579-591.
Becker, Gerhild, M.D. et al., "Peripherally Acting Opioid Antagonists in the Treatment of Opiate-Related Constipation: A Systematic Review," *Journal of Pain and Symptom Management* (Nov. 2007; accepted for publication Dec. 21, 2006); 34(5): 547.
Berge, Stephen M. et al., "Pharmaceutical Salts," *Journal of Pharmaceutical Sciences* (Jan. 1, 1977); 66(1): 1-19.
Bhounsule, Sushama A. et al., "Gastrointestinal actions of buprenorphine: are different receptors involved?" *European Journal of Pharmacology* (Dec. 1, 1996); 361(2-3):253-256.
Camilleri, M. "Current and future pharmacological treatments for diarrhea-predominant irritable bowel syndrome," *Expert Opinion on Pharmacotherapy* (Jun. 1, 2013); 14(9):1151-1160.
Cuer, J. C. et al., "Effects of Buprenorphine on Motor Activity of the Sphincter of Oddi in Man," *Eur J Clin Pharmacol* (Feb. 1, 1989); 36:203-204.
Feinberg, Andrew et al., "The opiate receptor: A model explaining structure-activity relationships of opiate agonists and antagonists," *Proc. Natl. Acad. Sci. USA* (Nov. 1, 1976); 73(11):4215-4219.
Haddad, Nizar et al., "Synthesis of a salbutamol dimer," *Tetrahedron Letters* (Feb. 11, 2002); 43(7):1135-1137.
Holzer, Peter, "New approaches to the treatment of opioid-induced constipation," *Eur Rev Med Pharmacolo Sci.* (Aug. 1, 2008); 12(0 1): 119-127.

(Continued)

*Primary Examiner* — Charanjit Aulakh
(74) *Attorney, Agent, or Firm* — Mintz, Levin, Cohn, Ferris, Glovsky and Popeo, P.C.

(57) ABSTRACT

Pharmaceutically active homo-dimers of opioid and other pharmaceutically active agents characterized by a single phenolic hydroxyl group wherein the respective monomers are ether-linked through such groups by an ethylene residue. The dimers share the receptor pharmacology of the corresponding monomer, in particular cases are non-absorbed, and the ether link of the dimers is particularly resistant to metabolism when administered to a subject, all conferring divers advantages relative to the corresponding monomers. Exemplary of the dimers are those of buprenorphine, naloxone, naltrexone, des-venlafaxine, albuterol and acetaminophen.

10 Claims, 20 Drawing Sheets

(56) References Cited

OTHER PUBLICATIONS

Koppert, Wolfgang et al., "Different profiles of buprenorphine-induced analgesia and antihyperalgesia in a human pain model," *Pain* (Jun. 5, 2005); 118:15-22.

Richards, Ryan, "Opioid Analgesics" (www.faculty.smu.edu): "A free phenol group is crucial for analgesic activity." (Oct. 29, 2015); 51 pages.

Rumack, Barry H., M.D. et al., "Acetaminophen Poisoning and Toxicity," *Pediatrics* (Jun. 1, 1975); 55:871-876.

Startiz, M. et al., "Effect of modern analgesic drugs (Tramadol, pentazocine, and buprenorphine) on the bile duct sphincter in man," *Gut* (May 1, 1986); 27:567-569.

Thorpe, David H., M.D., "Opiate Structure and Activity—A Guide to Understanding the Receptor," *Anesth Analg.* (Feb. 1, 1984); 63:143-151.

Zakko, S. et al., "Randomised clinical trial: the clinical effects of a novel neurokinin receptor antagonist, DNK333, in women with diarrhea-predominant irritable bowel syndrome," *Alimentary Pharmacology & Therapeutics* (Apr. 20, 2011); 33(12):1311-1321.

\* cited by examiner

Synthesis of Buprenorphine Dimer HCl Salt

Synthesis of the Naloxone Dimer HCl Salt

Synthesis of the Naltrexone Dimer HCl Salt

Synthesis of the Des-venlafaxine HCl Salt

Des-Venlafaxine dimer
5

Synthesis of the Acetaminophen Dimer

Synthesis of the Albuterol Dimer

Stability of the buprenorphine dimer when exposed to CYP enzymes in the presence and absence of a cofactor Stability of the buprenorphine dimer to aqueous conditions, as well as acidic and basic condition, each at room temperature and at 140°F for the indicated period of time.

Results of buprenorphine dimer receptor binding experiments – µ receptor

Results of buprenorphine dimer receptor binding experiments – κ receptor

μ agonist functional assay results for the buprenorphine dimer

µ antagonist functional assay results for the buprenorphine dimer

Results of oral and IV bioavailability of the buprenorphine dimer

Stress-induced fecal output of male CD-1 mice

Effect of the buprenorphine dimer on gastrointestinal motility in post inflammatory models Lack of release or formation of naloxone when the naloxone dimer is incubated with human microsomes Stability of the naloxone dimer salt to aqueous conditions, as well as acidic and basic condition, each at room temperature and at 140°F for the indicated period of time.

Results of the human µ opioid receptor binding assay of the naloxone dimer and naloxone Results of the naloxone dimer salt in alleviating loperamide-induced constipation in mice

PHARMACEUTICALLY ACTIVE DIMERS LINKED THROUGH PHENOLIC HYDROXYL GROUPS

CROSS-REFERENCES TO RELATED APPLICATIONS

This application claims the benefit of priority under 35 U.S.C. §119(e) to U.S. Provisional Application Ser. No. 61/985,207, filed Apr. 28, 2014; U.S. Provisional Application Ser. No. 62/101,768, filed Jan. 9, 2015; and U.S. Provisional Application Ser. No. 62/176,883, filed Jan. 9, 2015, the disclosures of each being incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Buprenorphine (Formula 1) is a semisynthetic opioid derivative of thebaine. It is a mixed agonist—antagonist opioid receptor modulator that is used to treat opioid addiction in higher dosages, to control moderate acute pain in non-opioid-tolerant individuals in lower dosages and to control moderate chronic pain in even smaller doses. Buprenorphine is absorbed in the gastrointestinal tract and acts systemically.

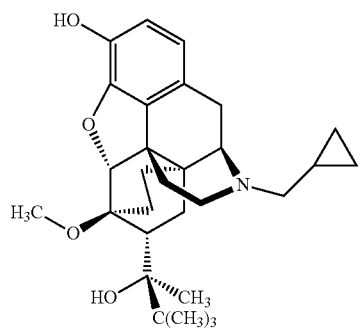

Formula 1

Naloxone (Formula 2) is a pure opioid antagonist. Naloxone is a medication used to reverse opioid-induced depression of the central nervous system, respiratory system, and hypotension. Naloxone may be combined with opioids that are taken by mouth to decrease the risk of their misuse. Naloxone is absorbed in the gastrointestinal tract and may act systemically, leading to opioid withdrawal symptoms.

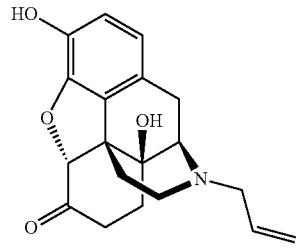

Formula 2

Naltrexone (Formula 3) is an opioid antagonist used primarily in the management of alcohol dependence and opioid dependence. It is marketed in generic form as its hydrochloride salt, naltrexone hydrochloride. It is also absorbed in the gastrointestinal tract and acts systemically. Like naloxone, naltrexone may induce opioid withdrawal symptoms.

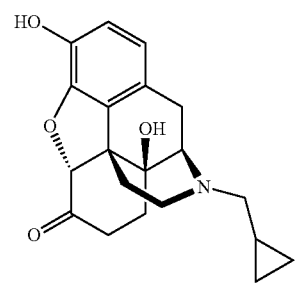

Formula 3

Des-venlafaxine (Formula 4) also known as O-desmethylvenlafaxine, is an antidepressant of the serotonin-norepinephrine reuptake inhibitor class. It has been considered for use in the treatment of chronic idiopathic constipation and gastroparesis, but because it acts systemically and its CNS effects can include sexual dysfunction its use for those purposes in persons not suffering from depression is contraindicated.

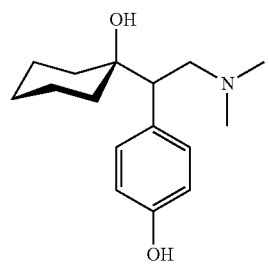

Formula 4

Acetaminophen (Formula 5), chemically named N-acetyl-p-aminophenol, is one of the most widely used medications in the United States. It is over-the-counter analgesic and antipyretic, commonly sold under the trade name Tylenol®. Acetaminophen is classified as a mild analgesic. It is commonly used for the relief of headaches and other minor aches and pains and is a major ingredient in numerous cold and flu remedies. In combination with opioid analgesics, acetaminophen can also be used in the management of more severe pain such as post-surgical pain and providing palliative care in advanced cancer patients. The quinone metabolite of acetaminophen is hepatotoxic. While usual dosing of acetaminophen is considered harmless, both acute and chronic overdoses can be fatal.

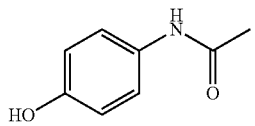

Formula 5

Albuterol (Formula 6) is a short-acting $\beta_2$-adrenergic receptor agonist used for the relief of bronchospasm in conditions such as asthma and chronic obstructive pulmonary disease. It relaxes muscles in the airways and increases air flow to the lungs. Albuterol is also used to prevent exercise-induced bronchospasm. It is usually given by inhalation to sidestep high first pass metabolism in the liver. Its highly variable bioavailability has been attributed to its phenolic hydroxyl group.

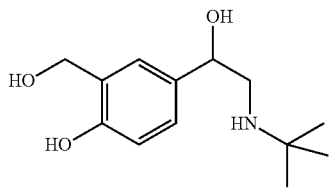

Formula 6

What these agents have in common is a single phenolic hydroxyl group. Such groups confer photo instability and undergo rapid presystemic or first pass metabolism in the gastrointestinal tract, variously forming sulfate esters or glucourinide esters. Buprenorphine and desvenlafaxine are also subjected to enzymatic degradation (CYP3A4 and CYP2A6). To sidestep consequent diminution in bioavailability, agents like buprenorphine and naloxone are most commonly administered by injection or sublingually.

Diarrhea-Predominant Irritable Bowel Syndrome (IBS-D)

IBS-D is a highly prevalent gastrointestinal disorder that is often accompanied, in addition to diarrhea, by both visceral hyperalgesia (enhanced pain from colorectal stimuli), discomfort, bloating, and gas.

Eluxadoline® (Forest Laboratories, Inc.) is a µ opioid receptor agonist and δ opioid receptor antagonist that has met primary endpoints of improvement in stool consistency and reduction of abdominal pain in Phase III testing, albeit without a demonstrable effect on reducing colonic hypersensitivity that results in hyperalgesia. Moreover, several cases of pancreatitis, a potentially life threatening disease, were reported in Phase II trials. Cases of pancreatitis were reported even after patients with a known history of biliary disease were excluded from clinical study enrollment. In general, µ agonists have a constricting effect on the Sphincter of Oddi, a muscular valve that regulates the flow of bile and pancreatic juice from the bile duct into the duodenum. It is very important that a drug with µ-receptor agonist activity and that is prescribed for long-term use, not lead to constriction of the Sphincter of Oddi.

There has accordingly been a long-standing need for a chronic treatment of IBS-D that decreases intestinal motility, thereby decreasing the incidence of diarrhea, is an analgesic, is not associated with pancreatitis, and more than merely treating symptoms, addresses underlying hypersensitivity and resulting hyperalgesia associated with IBS-D.

BRIEF SUMMARY OF THE INVENTION

We have discovered that dimerization of a defined group of pharmaceutically agents by O-alkylation through their phenolic hydroxyl groups, such that the active agent residues are bridged by an ethylene linker, yields distinct advantages relative to the active monomers, while preserving their receptor pharmacology.

In opioids and other pharmaceutical agents characterized by a single phenolic hydroxyl group, the covalent linkage of two such agents via such groups by the ethylene linker yields homo-dimers which are essentially more resistant to presystemic metabolism than their parent molecules. The ethylene linkage is highly stable and in particular cases yields other distinct advantages as well.

In the case of the opioid compounds buprenorphine, naloxone, and naltrexone the corresponding dimers are resistant to tampering, e.g., kitchen chemistry conversion to drugs of abuse; and are substantially non-absorbed in the GI tract, permitting their peripheral use without entering the central nervous system with consequent adverse effects such as addiction or opioid withdrawal.

The dimerization of des-venlafaxine prevents passage of the active agent across the blood brain barrier, and although the dimer is no longer effective in the treatment of depression, that requires CNS penetration, its functional ligands remain active and act locally in the intestinal tract, thus avoiding all centrally mediated adverse events, including sexual dysfunction. The dimerization, therefore, permits the agent to be safely utilized in the treatment of gastroparesis and chronic idiopathic constipation. The des-venlafaxine dimer is expected to function as a peripheral serotonin norepinephrine reuptake inhibitor. Unlike des-venlafaxine, the dimer is expected to act only peripherally in the gastrointestinal tract. Serotonin inherently has propulsive effect on the gastrointestinal tract and the dimer, therefore, could be used for treatment of intestinal conditions such as gastroparesis, chronic idiopathic constipation and pseudointestinal obstruction (ileus).

The effect of dimerizing acetaminophen, according to the invention, is to prevent formation of the quinone metabolite of the parent compound, which is hepatotoxic in acute and chronic use. In addition, blocking the phenolic hydroxyl of the monomer, dimerization reduces the ionic nature of the active agent, potentially enhancing transport through the blood-brain barrier and hence, analgesia.

Dimerization of albuterol enhances resistance to gastrointestinal and hepatic metabolism, increasing bioavailability of the drug when taken orally for the treatment of bronchospasm, which occurs in various pulmonary conditions, including asthma and chronic obstructive pulmonary disease.

In at least the case of morphinan compounds and until the present time, conventional thought seems to have been, when derivatizing active agents in search of, e.g., prodrug activity, phenolic hydroxyl groups were to be avoided test receptor binding be affected adversely. Surprisingly, the compounds of the invention are believed to retain their characteristic activities despite derivatization involving the phenolic hydroxyl groups of the corresponding monomers.

BRIEF DESCRIPTION OF THE DRAWINGS

In FIG. 6, DHP is DHP is dihydropyran, t-BuNH$_2$ is tert-butyl amine, TBSCI is tert-butyldimethylsilyl chloride; LAH is Lithium aluminium hydride; (Boc)$_2$O is tert-butyl dicarbonate; and AcOH is acetic acid.

DETAILED DESCRIPTION OF THE INVENTION

Pharmaceutical Compositions of the Dimers

General

Figure 1:
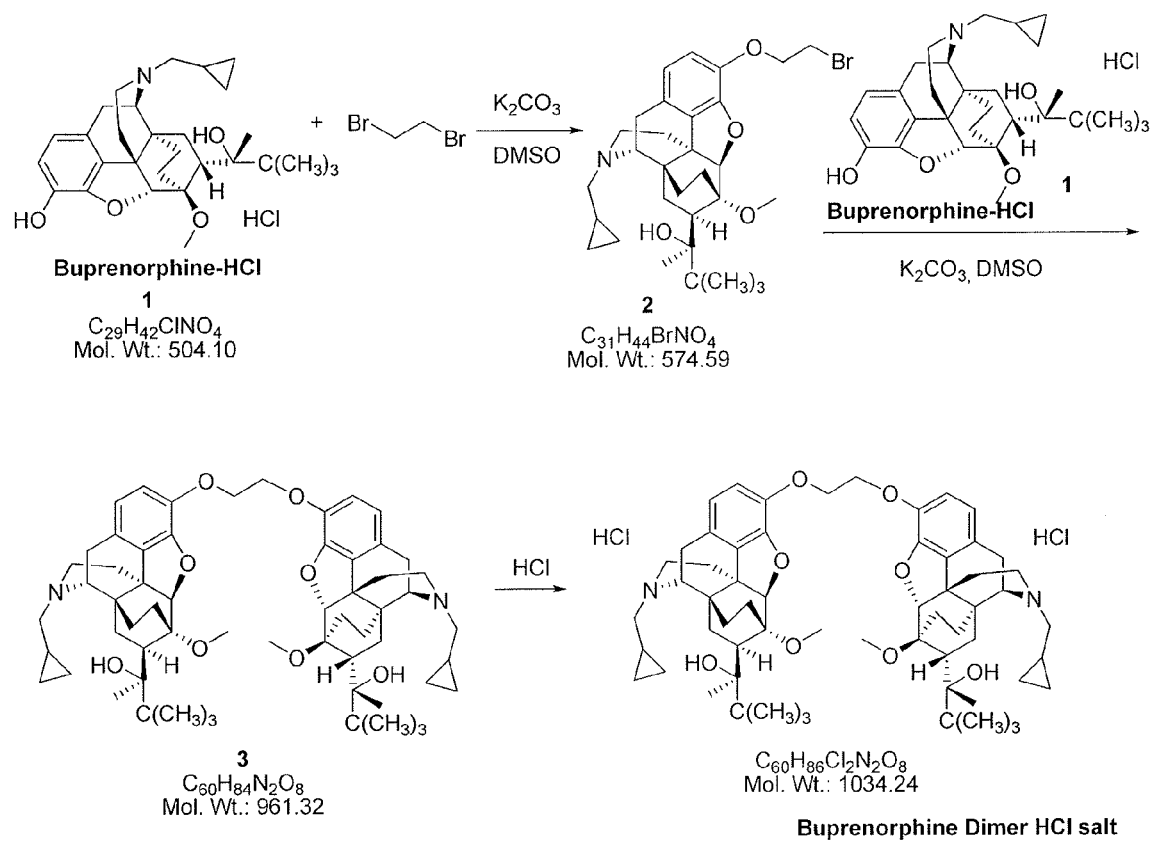
FIG. 1 provides a synthetic route to buprenorphine dimer HCl salt.

In certain embodiments, provided herein are pharmaceutical compositions comprising the dimers. A pharmaceutical composition can further comprise a pharmaceutically acceptable carrier. Illustrative pharmaceutically acceptable carriers and formulations are described below.

As will be appreciated, a pharmaceutically acceptable salt of a dimer may be used instead of or in addition to a dimer in any or all of the compositions and methods of treating discussed herein. Thus, in specific embodiments, a pharmaceutically acceptable salt of the dimer (i.e., any pharmaceutically acceptable salt of any of the dimers) is used in the methods of the invention. These salts can be prepared, for example, in situ during the final isolation and purification of the compound or by separately reacting the purified compound in its free base form with a suitable organic or inorganic acid and isolating the salt thus formed. In some embodiments, the pharmaceutically acceptable salt of the dimer is prepared using acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. For further description of pharmaceutically acceptable salts that can be used in the methods described herein see, for example, S. M. Berge et al., "Pharmaceutical Salts," 1977, *J. Pharm. Sci.* 66:1-19, which is incorporated herein by reference in its entirety.

The dimers of the invention can exist in unsolvated as well as solvated forms with pharmaceutically acceptable solvents such as water, ethanol, and the like. In general, the solvated forms are considered equivalent to the unsolvated forms for the purposes of the present invention. In a specific embodiment, the solvated form of the dimer is a hydrate.

In general, salt formation may improve shelf life of the resultant therapeutic agent. Appropriate salt synthesis can afford products that are crystalline, less prone to oxidation and easy to handle. Various salts can be prepared that would afford stable and crystalline compounds. A few examples are hydrochloric, sulfuric, p-toluenesulfonic, methanesulfonic, malonic, fumaric, and ascorbic acid salts.

In certain specific embodiments, such a pharmaceutical composition is formulated as oral tablet or capsule, extended release oral tablet or capsule (hard gelatin capsule, soft gelatin capsule), sublingual tablet or film, or extended release sublingual tablet or film. Illustrative pharmaceutically acceptable carriers and formulations are described in more detail below.

Pharmaceutical Compositions, Dosing and Routes of Administration

The dimers provided herein can be administered to a subject orally in the conventional form of preparations, such as capsules, microcapsules, tablets, granules, powder, troches, pills, suppositories, oral suspensions, syrups, oral gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol).

EXAMPLES

The following examples are offered to illustrate, but not to limit the claimed invention.

Example 1

Buprenorphine Dimer HCl Salt

The buprenorphine dimer was synthesized as shown in FIG. 1.
Synthesis of Intermediate 2:
Buprenorphine HCl-salt (5.0 g, 10.68 mmol, 1 equiv) and potassium carbonate (42.73 mmol, 4 equiv) were charged in a 3-neck round bottom flask followed by anhydrous DMSO (50 ml, 10 vol). The mixture was heated to 60° C. and 1,2-dibromoethane (3.7 mL, 42.72 mmol, 4 equiv) was added slowly. The reaction mixture was stirred at 60° C. for 16 h then cooled to room temperature, diluted with water and extracted with dichloromethane. The organic layer was washed with brine, dried (anh. $Na_2SO_4$), filtered and concentrated under reduced pressure to afford a viscous liquid. The crude product was purified by silica gel chromatography using 0-5% MeOH/DCM to afford 4.2 g (69%) intermediate 2 as off-white foamy solid.
Synthesis of Intermediate 3:
Buprenorphine HCl-salt (1.74 g, 3.72 mmol) and potassium carbonate (2.0 g, 14.87 mmol, 4 equiv) were charged in a 3-neck round bottom flask followed by anhydrous DMSO (10 mL). The mixture was heated to 60° C. and intermediate 2 (3 g, 5.22 mmol, 1.4 equiv) dissolved in 7 mL of anhydrous DMSO was added dropwise over a period of 2 h. The reaction mixture was stirred at 60° C. for 16 h then cooled to room temperature, diluted with water and extracted with dichloromethane. The organic layer was washed with brine, dried (anh. $Na_2SO_4$), filtered and concentrated under reduced pressure to afford a viscous liquid. The crude product was purified by silica gel chromatography using 0-5% MeOH/DCM to afford dimer 3 as a foamy solid (2.8 g, 77%).
Synthesis of the Dimer HCl Salt:
5.5 g (5.7 mmol) of bi-conjugate 3 was dissolved in 50 mL of ethyl acetate at room temperature under nitrogen. 3.43 mL (6.9 mmol, 1.2 equiv) of 2N HCl in ether was added dropwise at room temperature. The reaction mixture was stirred at room temperature for an additional hour and filtered to obtain the solid. The solid was further washed with 100 mL of ethyl acetate and dried under vacuum to give white solid (5.8 g, 98%). $^1$H NMR (300 MHz, DMSO-$d_6$): δ 9.75 (br, 2H), 6.88 (d, J=9.2 Hz, 2H), 6.67 (d, J=9.2 Hz, 2H), 4.66 (s, 2H), 4.23-4.42 (m, 4H), 3.84-3.92 (m, 2H), 3.40 (s, 6H), 3.21-3.35 (m, 5H), 2.98-3.20 (m, 7H), 2.64-2.85 (m, 4H), 2.12-2.26 (m, 4H), 1.72-1.94 (m, 4H), 1.38-1.52 (m, 4H), 1.26 (s, 6H), 0.99 (s, 20H), 0.48-0.76 (m, 10H), 0.32-0.42 (m, 4H); MS: m/z 962 (M+1)$^+$

Example 2

In Vitro Assay

Metabolic Stability of Buprenorphine Dimer

Incubations of the dimer (e.g., 1 µM) with human liver microsomes (e.g., 1 mg protein/mL) were carried out using a Tecan Liquid Handling System (Tecan), or equivalent, at 37±1° C. in 0.2-mL incubation mixtures (final volume) containing potassium phosphate buffer (50 mM, pH 7.4), $MgCl_2$ (3 mM) and EDTA (1 mM, pH 7.4) with and without a cofactor, NADPH-generating system, at the final concentrations indicated in a 96-well plate format. The NADPH-generating system consisted of NADP (1 mM, pH 7.4), glucose-6-phosphate (5 mM, pH 7.4) and glucose-6-phosphate dehydrogenase (1 Unit/mL). The buprenorphine dimer was dissolved in aqueous methanolic solution (methanol 0.5% v/v, or less). Reactions were started typically by addition of the cofactor, and stopped at four designated time points (e.g., up to 120 min) by the addition of an equal volume of stop reagent (e.g., acetonitrile, 0.2 mL containing an internal standard). Zero-time incubations served as 100% value to determine percent loss of substrate. Incubations were carried out in triplicate with an exception for zero-time samples (which were incubated in quadruplicate). Zero-cofactor (no NADPH) incubations were performed at zero-time and the longest time point. The samples were subjected to centrifugation (e.g., 920×g for 10 min at 10° C.) and the supernatant fractions analyzed by LC-MS/MS. Additional incubations were carried out with microsomes and a marker substrate (e.g., dextromethorphan to monitor substrate loss) as a positive control to determine if the test system was metabolically competent.

The above samples were analyzed by an LC-MS/MS method. Analysis was performed for the samples at each incubation solution. Results were determined by a comparison of peak ratios over the time course of the experiment (typically reported as "% Parent Remaining").

Data were calculated with a LIMS (includes Galileo, Thermo Fisher Scientific Inc. and reporting tool, Crystal Reports, SAP), the spreadsheet computer program Microsoft Excel (Microsoft Corp.) or equivalent. The amount of unchanged parent compound was estimated (to determine approximate percent substrate remaining in each incubation) based on analyte/internal standard (IS) peak-area ratios using a LIMS, Analyst Instrument Control and Data Processing Software (AB SCIEX), or equivalent.

Figure 7:
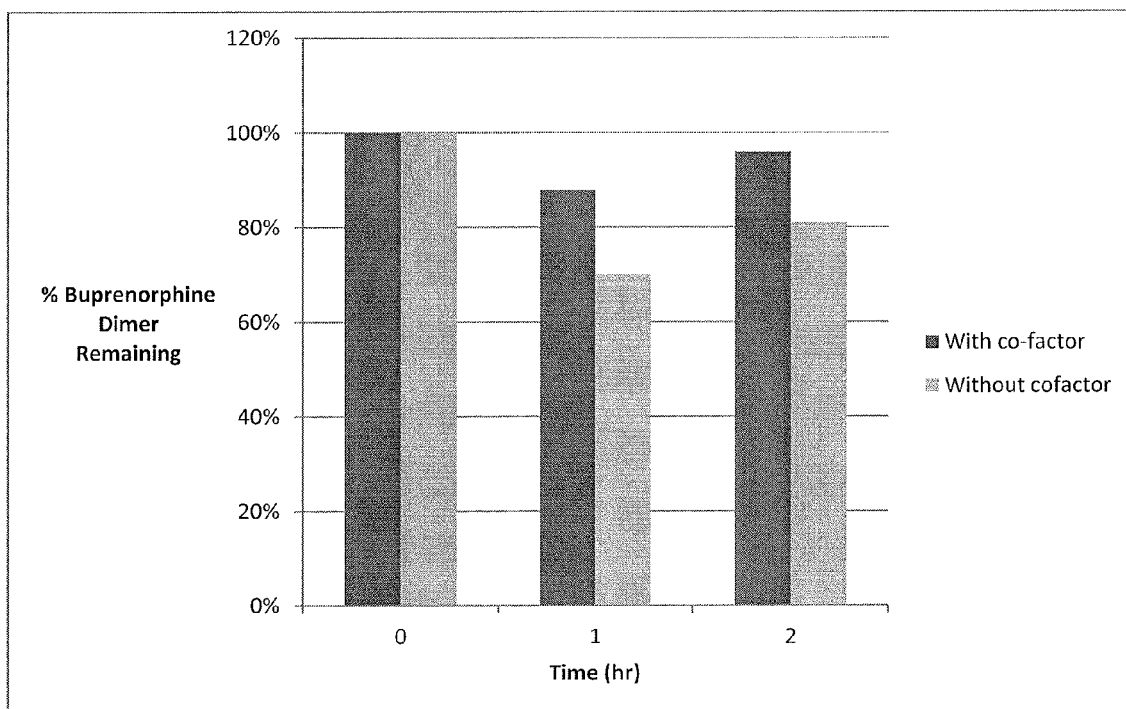
FIG. 7 provides a bar chart illustrating the stability of the buprenorphine dimer when exposed to CYP enzymes in the presence and absence of a co-factor.

Results:
Results are shown in FIG. 7 and indicate that the buprenorphine dimer was relatively stable in presence of microsomal enzymes for the duration of the assay. The microsomal enzymes are typically responsible for metabolism of drugs such as buprenorphine.

The dimer was stable in presence of the microsomes, with or without the co-factor. The assay was terminated at 2 hours because enzymes are typically not stable beyond 2 hours at incubation temperatures of 37° C.

Example 3

Stress Stability Assay of the Buprenorphine Dimer

This study facilitated the understanding of the ease with which a potential abuser could cleave the dimer using household chemicals such as baking soda, acid or simple heating in water. Buprenorphine dimer stability was assessed at room temperature in untreated tap water and in presence of acid (1N HCl) or base (5% aqueous sodium bicarbonate). The dimer was relatively stable under those conditions and under these conditions did not degrade to buprenorphine. See FIG. 8.

Figure 8:
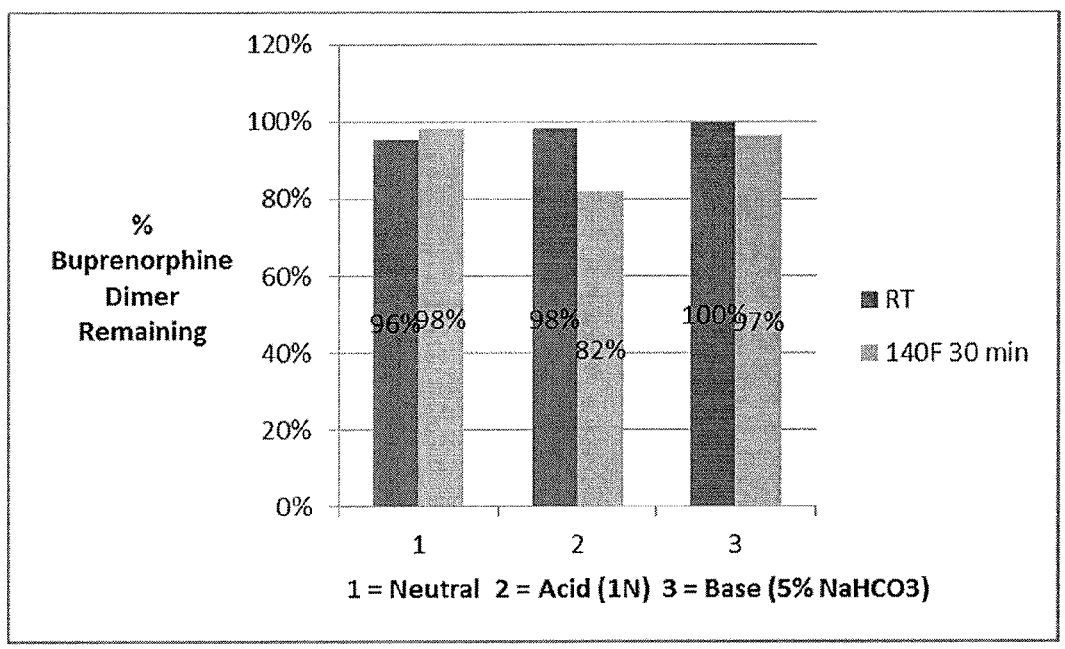
FIG. 8 provides a bar graph showing the stability of the buprenorphine dimer to aqueous conditions, as well as acidic and basic condition, each at room temperature and at 140° F. for the indicated period of time.

Results:
As shown in FIG. 8, the buprenorphine dimer remained stable and did not degrade to release buprenorphine either at room temperature or elevated temperature under extreme pH conditions even as long as 30 minutes.

These studies also facilitate the understanding of the stability of the dimer in the gastrointestinal tract which exhibits a gradient pH along its length in both patients with IBS-D and healthy subjects. The pH ranges from pH 1 due to excretion of hydrochloric acid from the parietal cells of the stomach to pH 8 in the colon. The proximal portion of the gastrointestinal tract is most acidic where the distal end is the least acidic.

Example 4

Receptor Binding Activity of the Buprenorphine Dimer

This example illustrates the binding of the buprenorphine dimer provided herein to the following receptors: μ-opioid receptor; κ-opioid receptor; and δ-opioid receptor.

Human μ Opioid Receptor Binding Assay

Membranes from Chinese Hamster Ovary cells expressing the human μ opioid receptor (Perkin Elmer #RBHOMM400UA) were homogenized in assay buffer (50 mM Tris, pH 7.5 with 5 mM MgCl2) using glass tissue grinder, Teflon pestle and Steadfast Stirrer (Fisher Scientific). The concentrates of the membranes were adjusted to 300 μg/mL in assay plate, a 96 well round bottom polypropylene plate. Compounds to be tested were solubilized in DMSO (Pierce), 10 mM, then diluted in assay buffer to 3.6 nM. In a second 96 well round bottom polypropylene plate, known as the premix plate, 60 μL of 6× compound was combined with 60 μL of 3.6 nM $^3$H-Naloxone. From the premix plate 50 μL was transferred to the assay plate containing the membranes, in duplicate. The assay plate was incubated for 2 h at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, underside sealed, and 30 μL Microscint 20 (Packard #6013621) was added to each well. A Topcount-NXT Microplate Scintillation Counter (Packard) was used to measure emitted energies in the range of 2.9 to 35 KeV. Results were compared to maximum binding, wells receiving no inhibitions. Nonspecific binding was determined in presence of 50 μM unlabeled naloxone. The biological activity of the buprenorphine dimer is shown in FIG. 9.

Figure 9:
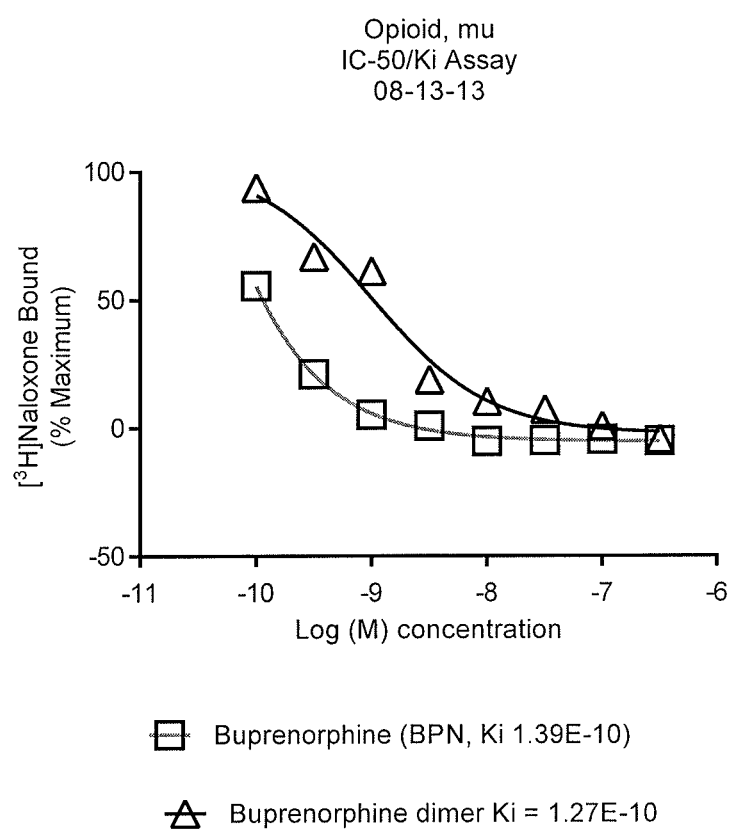
FIG. 9 provides the results of buprenorphine dimer receptor binding experiments—µ receptor.

Results:

The graph in FIG. 9 shows that the dimer has significant affinity for the opioid μ receptor The opioid μ receptor affinity of the buprenorphine dimer at $10^{-8}$M (~10 ng) was similar to that of buprenorphine.

Human κ Opioid Receptor Binding Assay

Membranes from cloned HEK-293 cells expressing the human κ opioid receptor (Amersham Biosciences UK Ltd. 6110558 200U) were homogenized in assay buffer (50 mM Tris, pH 7.5 with 5 mM MgCl2) using glass tissue grinder, Teflon pestle and Steadfast Stirrer (Fisher Scientific). The concentrates of the membranes were adjusted to 300 μg/mL in the assay plate, a 96 well round bottom polypropylene plate. Compounds to be tested were solubilized in DMSO (Pierce), 10 mM, then diluted in assay buffer to 3.6 nM. In a second 96 well round bottom polypropylene plate, known as the premix plate, 60 μL of 6× compound was combined with 60 μL of 3.6 nM $^3$H-Diprenorphine (DPN). From the premix plate 50 μL was transferred to the assay plate containing the membranes, in duplicate. The assay plate was incubated for 18 h at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, underside sealed, and 30 μL Microscint 20 (Packard #6013621) was added to each well. A Topcount-NXT Microplate Scintillation Counter (Packard) was used to measure emitted energies in the range of 2.9 to 35 KeV. Results were compared to maximum binding, wells receiving no inhibitions. Nonspecific binding was determined in the presence of 50 μM unlabelled naloxone. The biological activity of the buprenorphine dimer is shown in FIG. 10.

Figure 10:
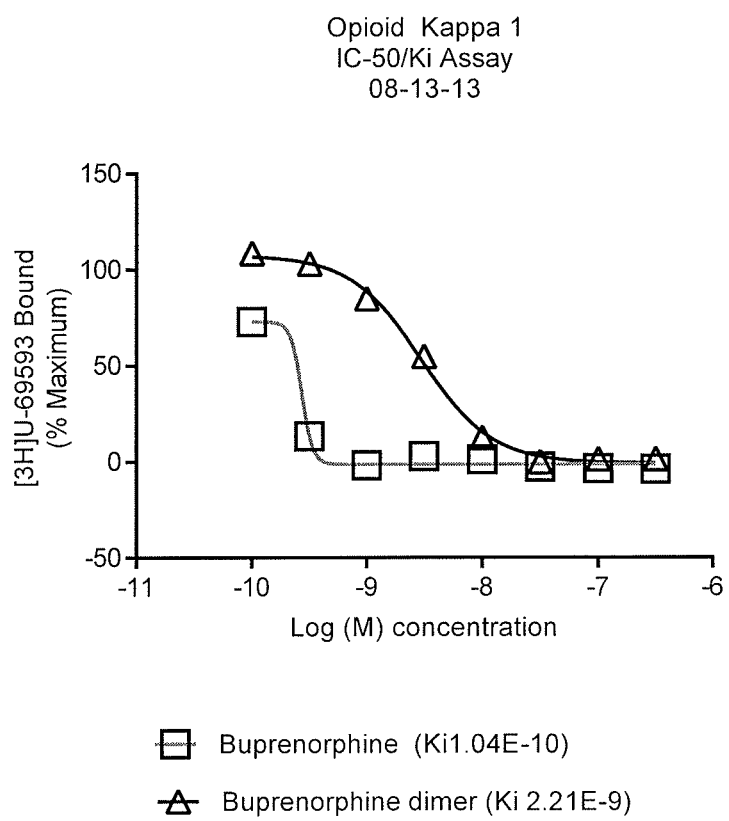
FIG. 10 provides the results of buprenorphine dimer receptor binding experiments—κ receptor.

Results:

FIG. 10 describes the opioid κ receptor agonist profile of the buprenorphine dimer. Neither the monomer nor the dimer of buprenorphine lost its affinity for the κ receptor. Qualitatively, as with buprenorphine, the binding of the buprenorphine dimer to opioid κ receptor increases with concentration. It is estimated that at about 1 μg, the opioid κ receptor affinity of the dimer was similar to that of buprenorphine.

Human δ Opioid Receptor Binding Assay

The assay was designed to test the ability of a compound to interfere with the binding of tritiated naltrindole to the human δ subtype 2 opioid receptor. Membranes from Chinese Hamster Ovary cells expressing the human δ subtype 2 opioid receptor (Perkin Elmer #RBHODM400UA) were homogenized in assay buffer (50 mM Tris, pH 7.5 with 5 mM MgCl$_2$) using a glass tissue grinder, Teflon pestle and Steadfast Stirrer (Fisher Scientific). The concentration of membranes was adjusted to 100 μg/mL in the assay plate, a 96 well round bottom polypropylene plate. Compounds to be tested were solubilized in DMSO, 10 mM, then diluted in assay buffer to 6× the desired final concentration. The ligand, $^3$H-natrindole (Perkin Elmer #NET-1065) was also diluted in assay buffer to 6 nM. Aliquots of $^3$H-natrindole (50 μL) were transferred to the assay plate containing the membranes in duplicate. The assay plate was incubated for 30 minutes at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, the underside sealed, and a 30 μL MictoS=scint 20 (Packard #6013621) was added to each well. A Topcount-NXT Microplate Scintillation Counter (Packard) was used to measure emitted energies in the range of 2.9 to 35 KeV. Results are compared to maximum binding, wells receiving no inhibitors. Nonspecific binding was determined in the presence of 1 μM unlabelled Natrindole. The biological activity of the buprenorpine dimer is 7.6 nM (IC50) and 2.87 (Ki). Relative to the μ and κ opioid receptors, the dimer has poor affinity for the δ receptor.

Example 5

Receptor Stimulation Activity μ Opioid Receptor Agonist and Antagonist Functional Assays: [$^{35}$S]GTPγS Binding Assay in Chinese Hamster Ovaries Expressing Human μ Receptors (CHO-hMOR) Cell Membranes This example illustrates the ability of the buprenorphine dimer provided herein to stimulate the p-opioid receptor-mediated signaling. Briefly, CHO-hMOR cell membranes were purchased from Receptor Biology Inc. (Baltimore Md.). About 10 mg/ml of membrane protein was suspended in 10 mM TRIS-HCl pH 7.2, 2 mM EDTA, 10% sucrose, and the suspension kept on ice. One mL of membranes was added to 15 mL cold binding assay buffer containing 50 mM HEPES, pH 7.6, 5 mM MgCl$_2$, 100 mM NaCl, 1 mM DTT and 1 mM EDTA. The membrane suspension was homogenized with a polytron and centrifuged at 3000 rpm for 10 min. The supernatant was then centrifuged at 18,000 rpm for 20 min. The pellet was resuspended in 10 mL assay buffer with a polytron.

The membranes were pre incubated with wheat germ agglutinin coated SPA beads (Amersham) at 25° C., for 45 min in the assay buffer. The SPA bead (5 mg/ml) coupled with membranes (10 µg/ml) was then incubated with 0.5 nM [$^{35}$S] GTPγS in the assay buffer. The basal binding is that taking place in absence of added test compound; this unmodulated binding was considered as 100%, with agonist stimulated binding rising to levels significantly above this value. A range of concentrations of receptor agonist SNC80 was used to stimulate[$^{35}$S]GTPγS binding. Both basal and non-specific binding were tested in the absence of agonist; non-specific binding determination included 10 µM unlabeled GTPγS.

The buprenorphine dimer was tested for function as an antagonist by evaluating its potential to inhibit agonist-stimulated GTPγS binding using D-Phe-Cys-Tyr-D-Trp-Orn-Thr-Pen-Thr-NH2 (CTOP) as the standard. Radioactivity was quantified on a Packard Top Count. The following parameters are calculated:

% Stimulation=[(test compound cpm−non-specific cpm)/(basal cpm−non-specific cpm)]*100

% Inhibition=(% stimulation by 1 µM SNC80−% stimulation by 1 µM SNC80 in presence of test compound)*100/(% stimulation by 1 µM SNC80−100).

$EC_{50}$ was calculated using GraphPad Prism. Graphs for the compounds tested are shown in FIGS. 11 and 12.

Figure 11:
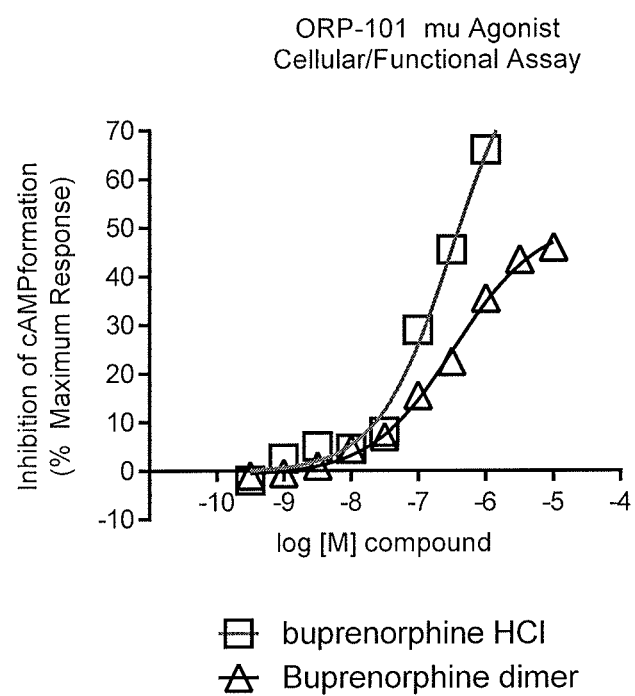
FIG. 11 provides µ agonist functional assay results for the buprenorphine dimer.
Figure 12:
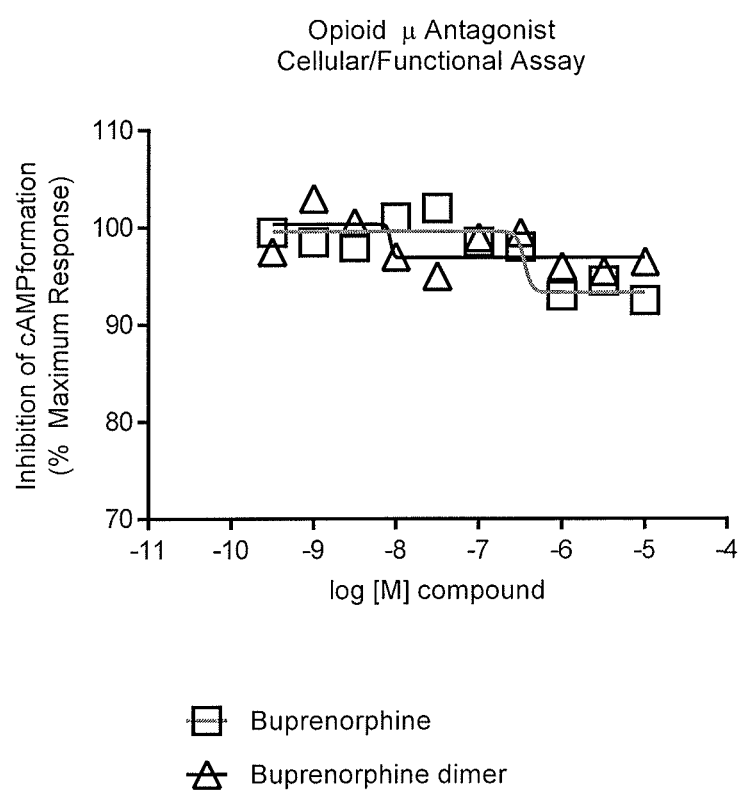
FIG. 12 provides µ antagonist functional assay results for the buprenorphine dimer.

Results:

Data shown in FIG. 11 indicates that the buprenorphine dimer is a potent µ agonist. The results also indicate that the opioid µ receptor activity of the dimer at $10^{-6}$M (~1 µg) is similar to that of buprenorphine. Data in FIG. 12 shows that the buprenorphine dimer does not function as a µ-antagonist.

Example 6

In Vivo Pharmacokinetic Study

Animals used in these animal pharmacokinetic studies were CD-1 mice (about 35 gms, n=3 per time point). Drugs tested were buprenorphine and the buprenorphine dimer. Dose 10 mg/kg IV and oral gavage. Blood was collected at time 0, 30 min and 1, 2, 6 and 24 hours. Blood samples for the drug were analyzed after harvesting the plasma and by LC/MS/MS as follows:

Standard curve was prepared in mouse plasma spiked with either the test drugs (10-25000 nM). Plasma samples (50 µL) were extracted in 300 µL acetonitrile containing losartan or buprenorphine-$d_4$ as internal standard. Extracts were centrifuged at 16000×g at 4° C. for 5 minutes. Supernatants (250 µL) were transferred to a new tube and dried under $N_2$ at 45° C. for 1 hour. Samples were reconstituted with 100 µL of 30% acetonitrile, vortexed and centrifuged. Supernatants (90 µL) were transferred to LC vials and 10 µL is injected on LC/MS.

Figure 13:
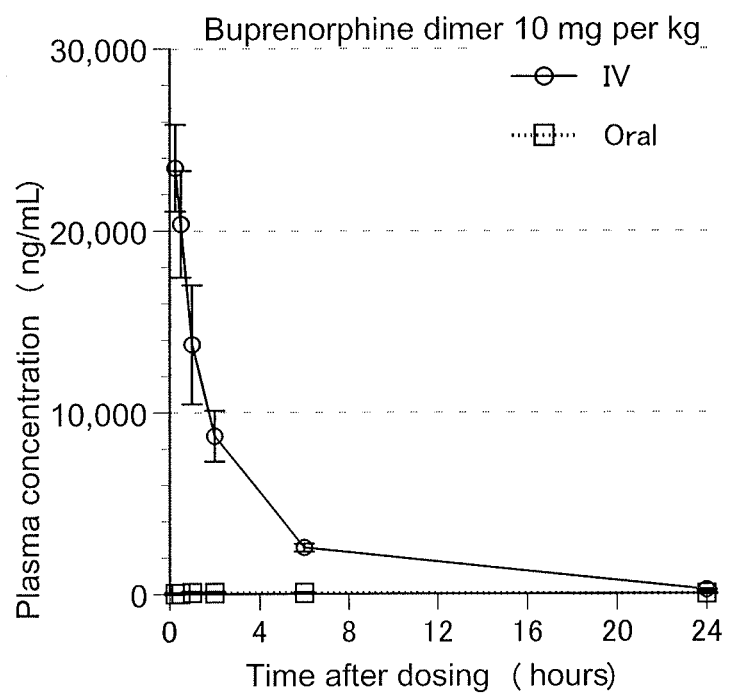
FIG. 13 provides the results of oral and IV bioavailability of the buprenorphine dimer FIG. 14 provides the graphs for stress-induced fecal output of male CD-1 mice according to the evaluation of Example 7.

Results:

FIG. 13 depicts the plasma concentration profiles of the dimer after 10 mg oral and IV dose. The graph indicates that the absolute bioavailability, measured as a ratio of the area under the concentration curve after oral and IV dose, of the dimer is 1% or less, whereas that of the monomer is about 30%.

Example 7

In Vivo Assay

Stress-Induced Fecal Output

The animals used in the studies were male CD-1 mice, average weight about 30 to 35 g, with an average of 5 mice per dose group. The mice were generally housed in colony housing where they are housed 3 per cage in polycarbonate cages with access to food and water ad lib.

On the day of the experiment the mice were transported to the procedure room where they were individually housed in 20 cm wide×20 cm deep×15 cm tall cages, equipped with a wire mesh bottom after intragastric administration of test compounds. During the test the animals were allowed access to water only ad lib. The wire mesh bottomed tall cage creates a novel environment which induces stress in mice. The number of pellets excreted was determined on an hourly basis. Results are shown in FIG. 14.

Figure 14:
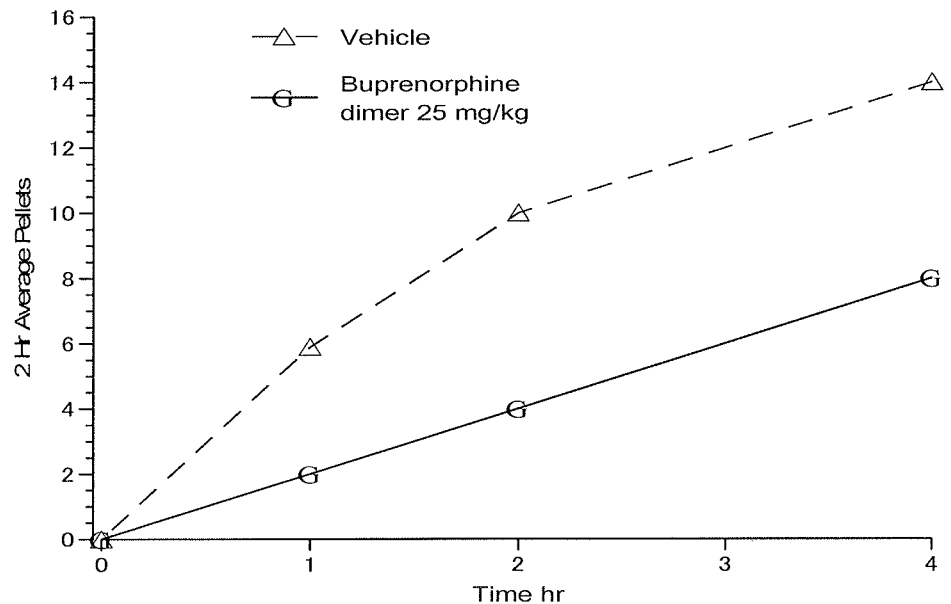
Figure 14:
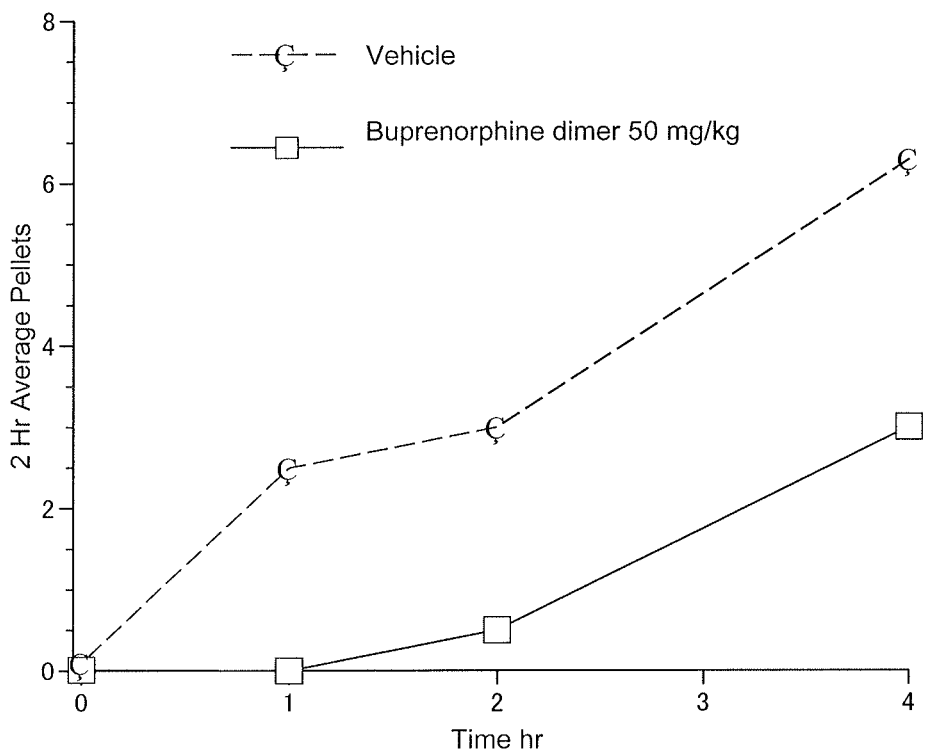
Figure 15:
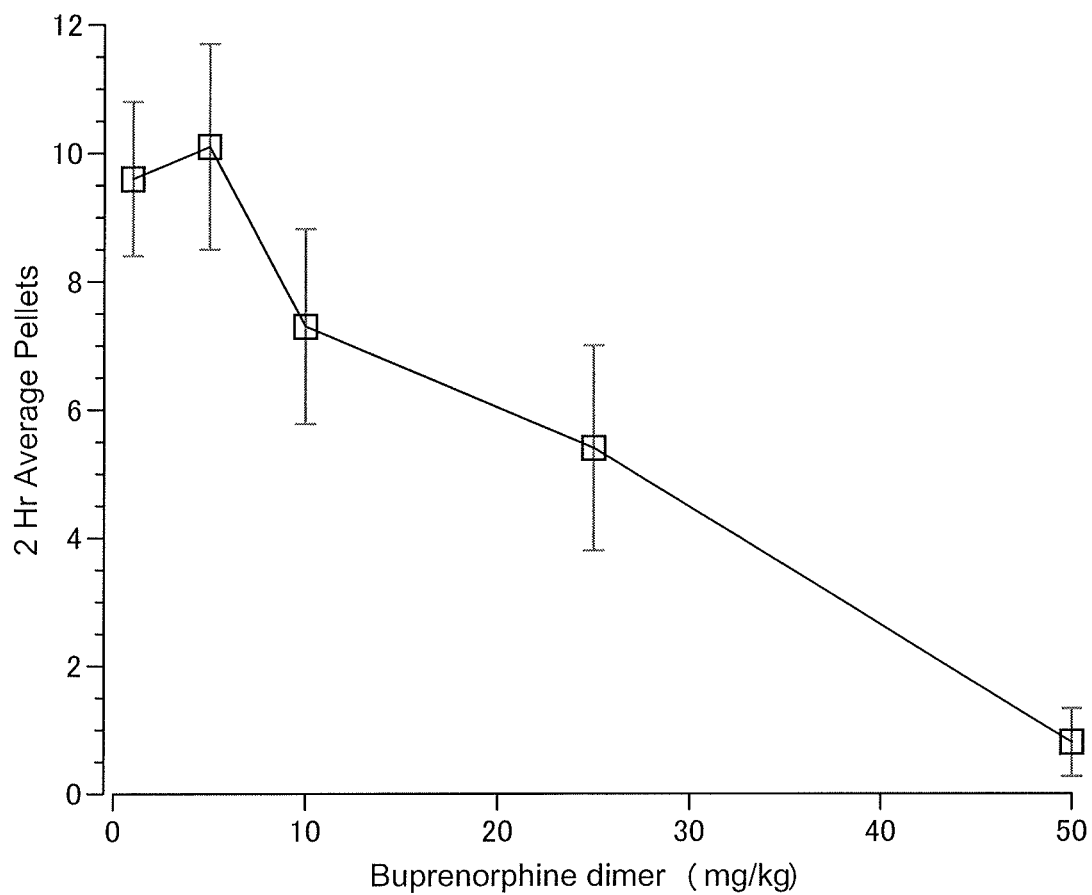
FIG. 15 shows the buprenorphine dimer decreases fecal output in a dose-dependent manner.

Results:

FIG. 14 shows that oral dose of the dimer significantly reduced the fecal output in mice versus placebo (vehicle). The doses investigated were 25 and 50 mg per kg of mice. The results do not change even when the animals with zero fecal output, suggesting extreme sensitivity, were removed from the analysis. FIG. 15 shows that fecal output in mice decreases with dose, which indicates a true pharmacological effect.

In Vivo Assay

Effect on Post-Inflammatory Altered GI Transit Time

This test was designed to measure the effect of test substance on gastrointestinal hypersensitivity following inflammation. Post-inflammatory altered GI transit was induced in male CD-1 mice by injecting freshly opened oil of mustard (95% pure allyl isothiocyanate, 0.5% in ethanol). The effect of stress on the post-inflammatory GI tract was tested 3-4 weeks after dosing. At this point, the GI tract was in a hypersensitive state, i.e., having a significantly greater response to stimuli (hyperalgesia). The effect of the test substance was measured after oral administration (intragastric gavage) and subjecting animals to environmental stress by housing them in cages (20 cm wide×20 cm deep×15 cm tall), equipped with a wire mesh bottom. During the test the animals were allowed access to water ad lib. The wire mesh bottomed tall cage creates a novel environment which induces stress in mice. The number of pellets excreted is determined on hourly to two-hourly basis. See FIG. 16.

Figure 16:
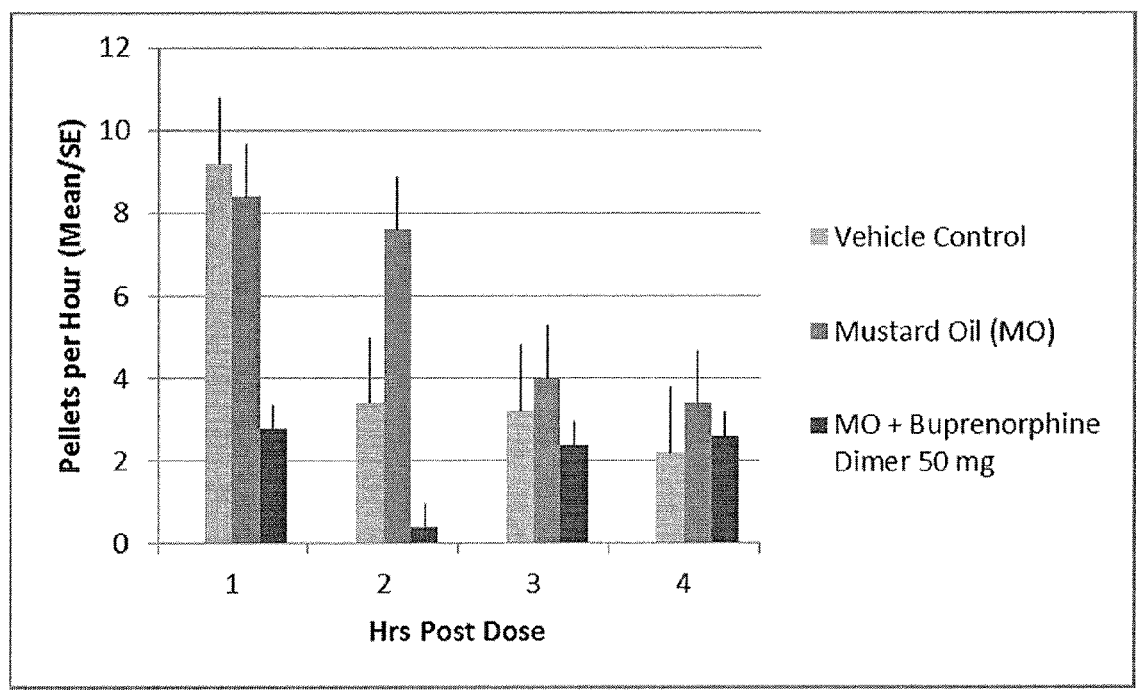
FIG. 16 shows the effect of the buprenorphine dimer on gastrointestinal motility in post inflammatory models according to Example 7.

Results:

As shown in FIG. 16, the buprenorphine dimer at 25 mg per kg significantly decreases gastrointestinal motility in this model as measured by fecal output. The graph also shows the fecal pellet output in the mice not treated with mustard oil is transient and does not last beyond 1 hour. The increase in pellet excretion in mustard oil treated animals persists even at 2 hours. The dimer continues to inhibit gastrointestinal motility with statistically significant results even at 2 hours.

Example 8

Naloxone and Naltrexone Dimer HCl Salts

Figure 2:
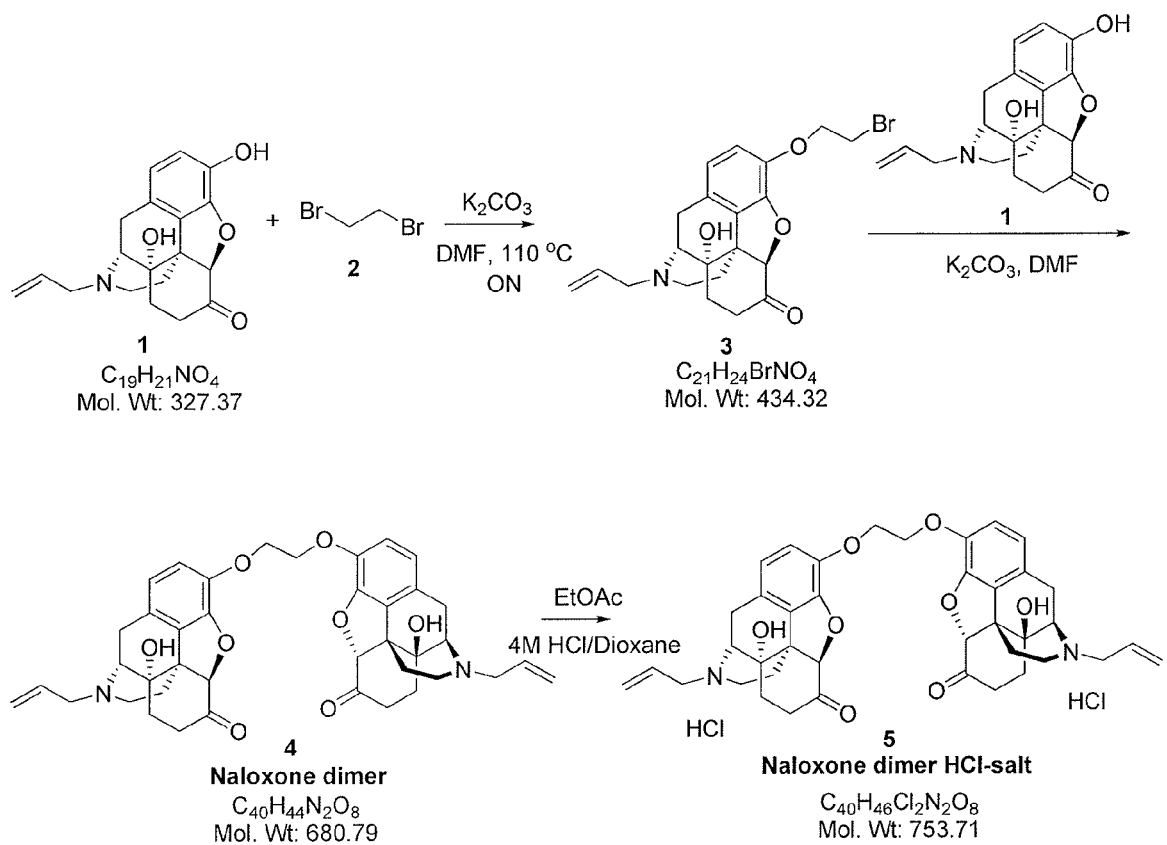
FIG. 2 provides a synthetic route to naloxone dimer HCl salt.

The naloxone dimer HCl salt was synthesized as shown in FIG. 2.

Synthesis of Intermediate 3:

Naloxone (5.0 g, 15.27 mmol, 1 equiv) and potassium carbonate (6.32 g, 45.8 mmol, 3 equiv) were charged to a 500-mL, 3-neck round bottom flask followed by anhydrous DMF (50 ml, 10 vol). The mixture was heated to 60° C. and 1,2-dibromoethane (6.57 mL, 76.35 mmol, 5 equiv) was added to the reaction mixture via syringe. The reaction mixture was stirred at 110° C. for 16 h. TLC analysis shows mostly intermediate 3. After the reaction was completed, the mixture was diluted with water (150 mL, 30 vol) and extracted with ethyl acetate (100 mL, 20 vol). The aq. layer was extracted with ethyl acetate (100 mL). The combined organic portions were washed with brine (100 mL), dried over magnesium sulfate and concentrated under reduced pressure. The crude product was purified by silica gel chromatography using 0-5% MeOH/DCM to afford intermediate 3 as viscous oil (1.25 g).

Synthesis of Intermediate 4:

Intermediate 3 (1.25 g, 2.87 mmol) and potassium carbonate (1.59 g, 11.52 mmol, 4 equiv) were charged into a 3-neck round bottom flask containing compound 1 (0.57 g in 15 mL DMF). The mixture was heated at 60° C. and the reaction progress was monitored by TLC. The mixture was cooled to room temperature, diluted with water and extracted with ethyl acetate (50 mL×2). The combined organic portions were dried over magnesium sulfate, filtered and concentrated under reduced pressure to afford yellow syrup. The crude product was purified by silica gel chromatography using 0-4% MeOH/DCM to afford naloxone dimer 4 as a pale white solid (0.55 g).

Synthesis of Naloxone Dimer HCl-Salt 5:

0.55 g (0.8 mmol) of bi-conjugate 4 was dissolved in 10 mL of ethyl acetate at room temperature under nitrogen. 0.8 ml (3.2 mmol, 4.0 equiv) of 4M HCl in dioxane was added drop-wise at room temperature. The reaction mixture was stirred at room temperature for an additional hour and filtered to obtain the solid. The solid was further washed with 20 mL of MTBE and dried under vacuum to obtain a white solid (0.5 g). HPLC analysis shows 98.2% purity (AUC) at 235 Nm. $^1$H NMR (300 MHz, DMSO-$d_6$): 1.41-1.63 (m, 4H, $CH_2$), 1.98 (d, 2H, $CH_2$), 2.14 (d, 2H, $CH_2$), 2.63 (dt, 2H, $CH_2$), 2.88-3.19 (m, 6H, $CH_2$), 3.26-3.44 (m, 6H, $CH_2$), 3.62 (d, 2H, CH), 3.72-3.84 (m, 2H, $CH_2$), 3.85-3.98 (m, 2H, CH), 4.41 (dd, 4H, $CH_2$), 5.09 (s, 2H, OH), 5.58 (dd, 4H, $CH_2$), 5.82-6.02 (m, 2H, CH), 6.78 (d, 2H, Ar), 6.90 (d, 2H, Ar), 9.42 (s, 2H, NHCl).

Figure 3:
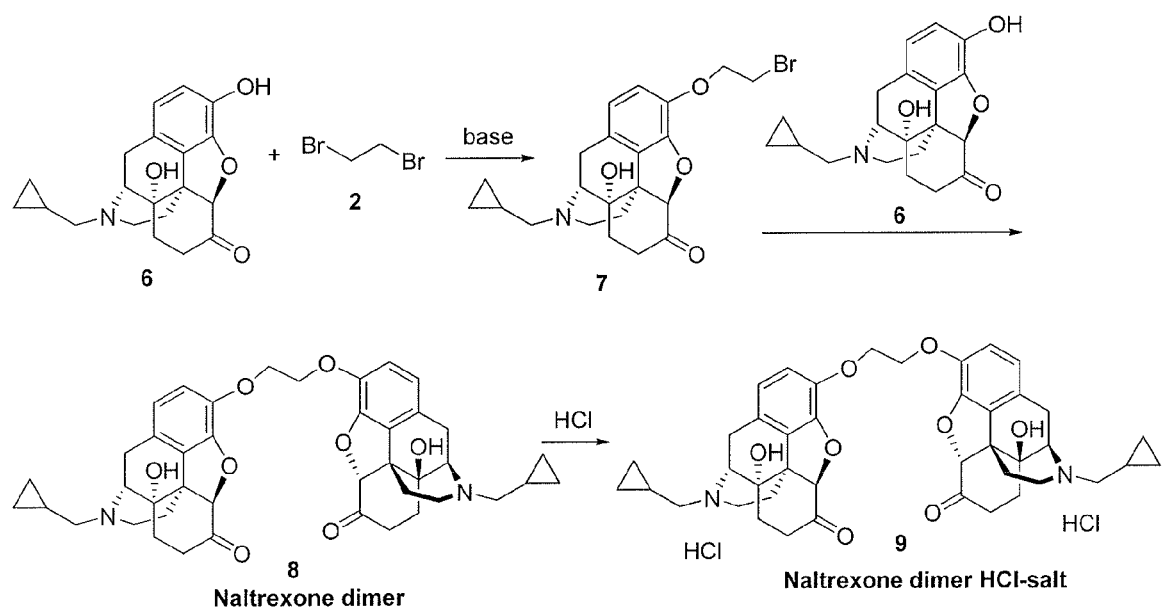
FIG. 3 provides a synthetic route to the naltrexone dimer HCl salt

The naltrexone dimer HCl salt is similarly synthesized, substituting for naloxone a molar equivalent of naltrexone, as shown in FIG. 3.

Example 9

Metabolic Stability of the Naloxone Dimer

Figure 17:
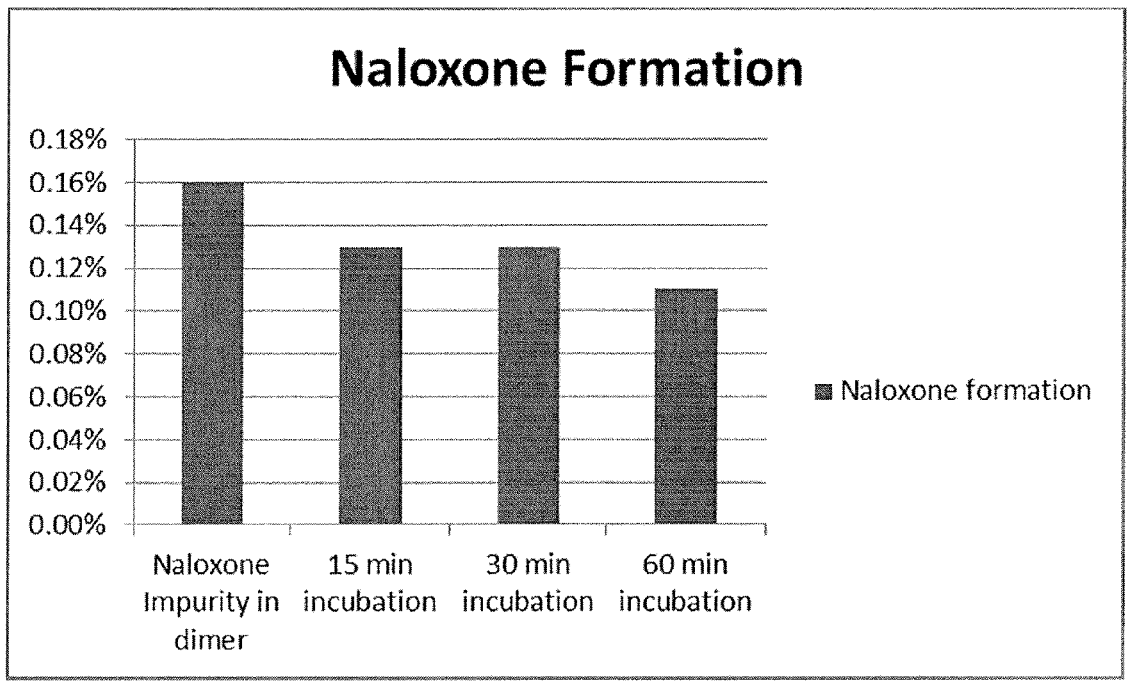
FIG. 17 provides a bar chart illustrating the stability of the naloxone dimer salt when exposed to CYP enzymes in the presence and absence of a co-factor.

Metabolic stability of the naloxone dimer was investigated using a protocol similar to the buprenorphine dimer experiment discussed in Example 3. Approximately 1 µM of the dimer was incubated with human liver microsomes (1 mg protein/ml) for up to 1 hour. The incubation medium was assayed by LC/MS/MS for the formation of naloxone over time. As shown in FIG. 17, there was no evidence of formation naloxone over time.

Example 10

Stress Stability of the Naloxone Dimer

Figure 18:
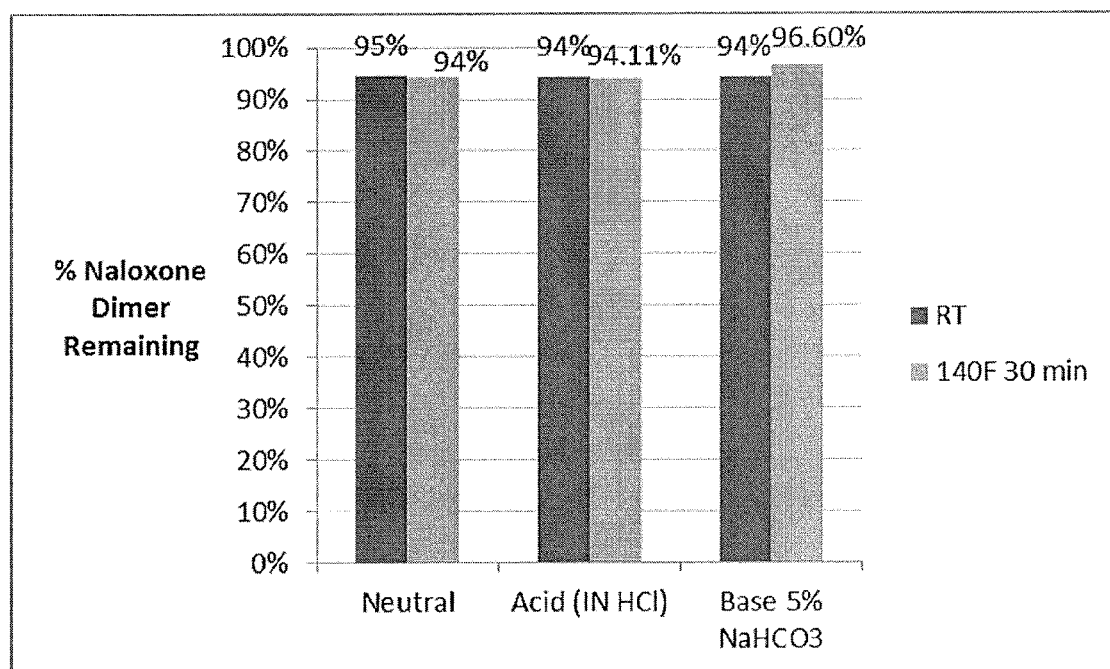
FIG. 18 provides a bar graph showing the stability of the naloxone dimer salt to aqueous conditions, as well as acidic and basic condition, each at room temperature and at 140° F. for the indicated period of time.

Naloxone dimer stability was assessed at room temperature in untreated tap water and in the presence of acid (1N HCl) or base (5% aqueous sodium bicarbonate). The protocol was similar to the buprenorphine dimer stress stability experiment described in Example 3. The dimer was relatively stable under those conditions and under the described conditions does not appreciably degrade to naloxone, as shown in FIG. 18.

Example 11

µ Receptor binding assay of the Naloxone Dimer HCl Salt

Figure 19:
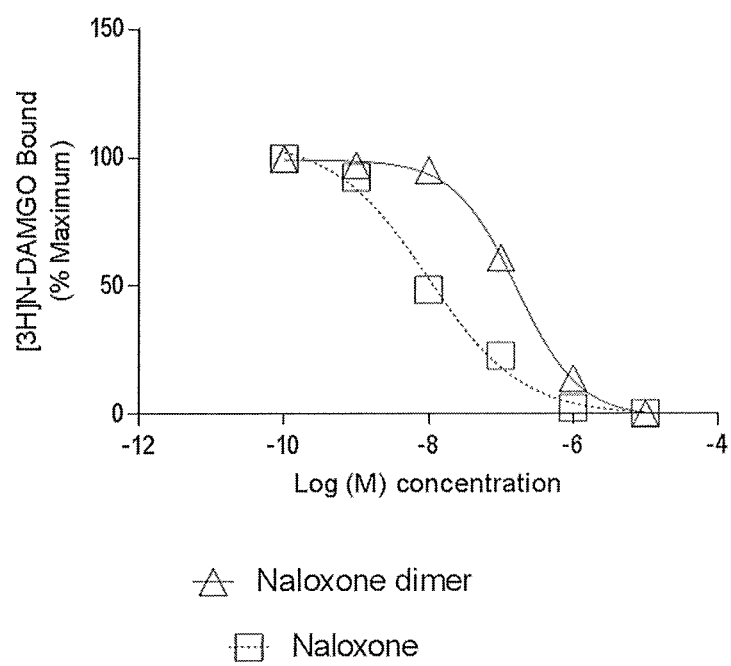
FIG. 19 provides the results of the human µ opioid receptor binding assay of the naloxone dimer and naloxone.

The experiment was designed to determine the inhibition of tracer DAMGO ([tyrosyl-3,5-$^3$H(N)]-[D-Ala$^2$, N-Me-Phe, Gly$^5$-ol]-Enkephalin acetate to the rat opiate µ receptor by naloxone ($10^{-10}$, $10^{-9}$, $19^{-8}$, $10^{-7}$, $10^{-6}$, and $10^{-5}$ mol/L) and naloxone dimer ($10^{-10}$, $10^{-9}$, $10^{-8}$, $10^{-7}$, $10^{-6}$, and $10^{-5}$ mol/L). The test materials were incubated at 25° C. for 60 min. The experiment was conducted with human µ opioid receptors previously bound to [3H]N-DAMGO. DAMGO is a peptide with a high affinity for human µ opioid receptor. As the concentration of naloxone or the naloxone dimer was increased it gradually replaced the DAMGO bound to the receptor and thus the downward slope of the curves as shown in FIG. 19. The binding affinities of naloxone, the naloxone dimer, and other similar antagonists are provided in Table 1.

TABLE 1

| Antagonist | Ki (nM) |
| --- | --- |
| Naloxone | 0.5 |
| Naloxone dimer | 4.5 |
| Pegylated naloxegol[1] | 5 |
| Methylnaltrexone Bromide[2] | 42 |

[1]Naloxegol ®, AstraZeneca, Briefing Document 6 May 2014 to the Anesthetic and Analgesia Advisory Committee to the FDA.
[2]Relistor ®, Salix Laboratories, Briefing Document 8 May 2014 to the Anesthetic and Analgesia Advisory Committee to the FDA.

Example 12

Constipation Assay of the Naloxone Dimer HCl Salt

Figure 20:
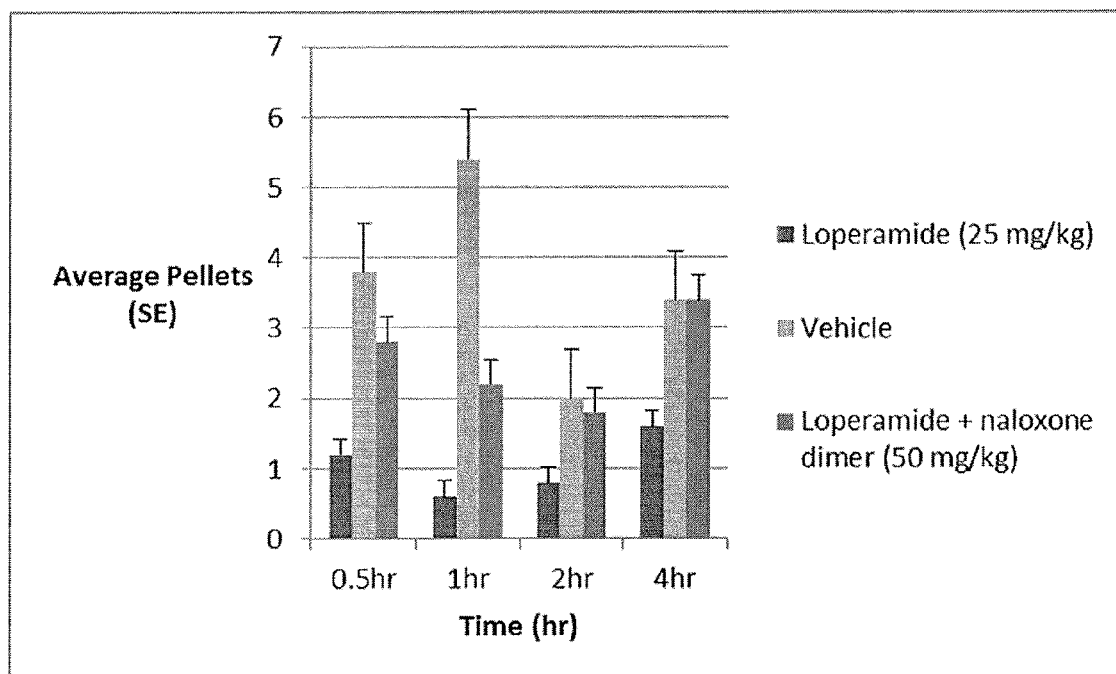
FIG. 20 provides a bar graph showing the effect of the naloxone dimer salt in alleviating loperamide-induced constipation in mice.

The naloxone dimer reversed the constipating effects of the opioid µ agonist loperamide, as shown in FIG. 20. In the study a group mice were subjected to mild stress, which normally induces diarrhea and gastrointestinal motility measured by number of fecal pellets excreted per hour. The number of pellets expelled by the group treated with loperamide is significantly less than the pellets excreted per hour by control (vehicle) animals. This observation confirms the constipating effects of loperamide. In the group where the effect of loperamide was reversed by naloxone dimer the number of pellets excreted per hour is more than the pellets excreted by loperamide-treated animals and comparable to those of the control animals by hour 3 or later. The results demonstrate that the naloxone dimer effectively reversed the constipating effects of the human µ opioid agonist loperamide.

The naloxone dimer offers significant benefit over naloxone, naltrexone, pegylated naloxone and methyl naltrexone as it is expected to act on the gastrointestinal tract receptors without being absorbed to treat opioid bowel disorder in general and opioid induced constipation in particular. The naloxone dimer can also find other therapeutic uses such as treatment of bloating, decreased gastric motility, abdominal cramping, and GERD (gastroesophagael reflex disease.

Example 13

Des-Venlafaxine Dimer HCl Salt

Figure 4:
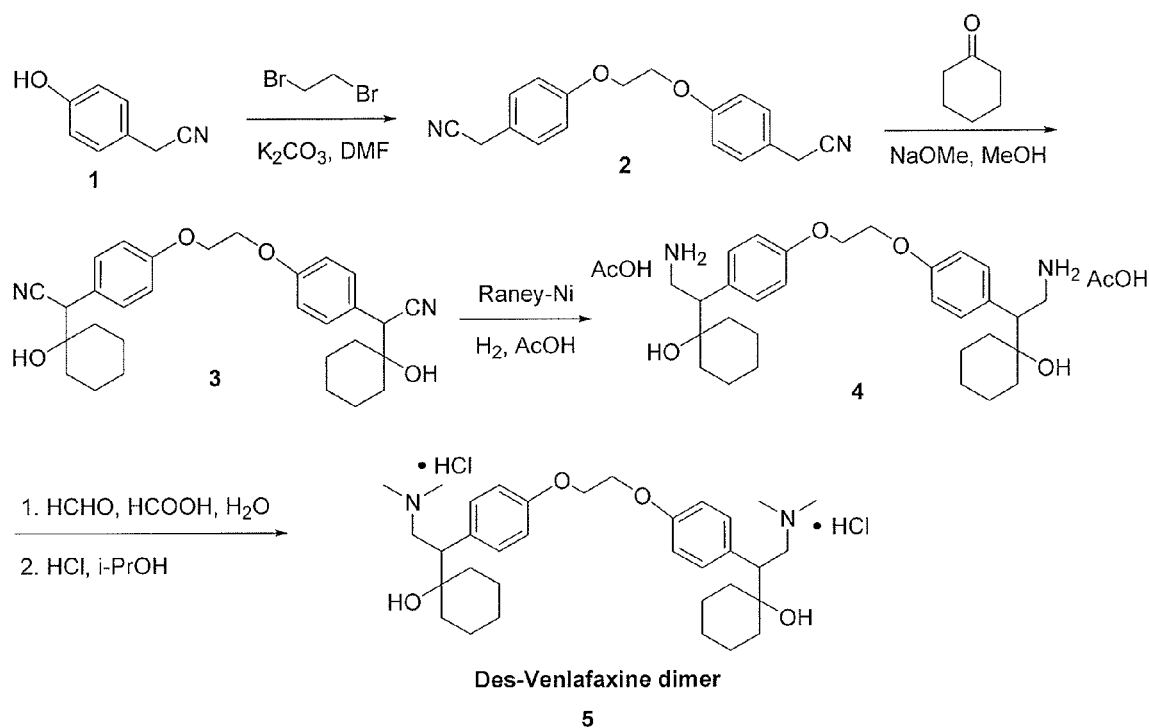
FIG. 4 provides a synthetic route to des-venlafaxine dimer HCl salt.

The compound was synthesized as shown in FIG. 4.
Synthesis of Compound 2.
Compound 1 (1 equiv) in DMF was reacted with 1,2-dibromoethane (2 equiv) in the presence of anhydrous potassium carbonate (3 equiv) at 60° C. for 15 hours. TLC analysis indicates complete consumption of the starting compound. The mixture was diluted with MTBE and washed with water. The organic phase was separated, dried over magnesium sulfate, filtered and concentrated. The crude product was purified by silica gel chromatography, affording pure product 2. Yield: 61%.

Synthesis of Compound 3.

Compound 2 (1 equiv) was added to sodium methoxide in methanol (5 equiv) at 5° C. and stirred at 0-5° C. for 2 hours. Cyclohexanone (2.5 equiv) was added and the mixture was stirred at 0-5° C. for 4 hrs. The reaction mixture was quenched with saturated ammonium chloride solution and concentrated. The resulting residue was dissolved in ethyl acetate and water. The organic phase was separated, dried over magnesium sulfate, filtered and concentrated. The crude product was purified by silica gel chromatography affording pure product 3. Yield: 74%.

Synthesis of Compound 4.

Raney Nickel (30 wt %) was added to a mixture of compound 3 (1 equiv) in acetic acid (6 vol). The mixture was flushed with hydrogen (30 psi) then stirred under 140-150 psi of hydrogen at 55° C. for 3 hours, then cooled to room temperature. The mixture was filtered through a pad of celite and the filtrate was concentrated. The residue was dissolved in water and washed with MTBE to remove any unreacted materials. The product was extracted into ethyl acetate after neutralizing with bicarbonate solution. The ethyl acetate layer was dried over magnesium sulfate, filtered and concentrated. The crude product was purified by silica gel chromatography affording pure product 4. Yield: 85%.

Synthesis of Compound 5.

To a stirred solution of 4 (1 equiv) in water was added 37-40% formaldehyde (12 equiv) and formic acid (6 equiv). The reaction mixture was heated at 100° C. for 22 hours then cooled to room temperature. The mixture was washed with MTBE then basified to pH 8-9 using 20% NaOH solution. The organic layer was dried over magnesium sulfate, filtered and concentrated. The crude product was purified by silica gel chromatography affording pure product 5. The product was dissolved in ethyl acetate and 2N HCl in ethyl acetate was added. The slurry was stirred for 30 minutes, filtered and dried to afford product 5. Yield: 79%. $^1$H NMR (300 MHz, DMSO-do): 0.96-1.58 (m, 20H, $CH_2$), 2.62 (s, 12H, $CH_3$), 2.94 (dd, 2H, CH), 3.45 (dd, 2H, CH), 3.63 (dd, 2H, CH), 4.22 (s, 2H, OH), 4.36 (t, 4H, $CH_2$), 6.76 (d, 4H, Ar), 7.06 (d, 4H, Ar).

Example 14

Acetaminophen Dimer

Figure 5:
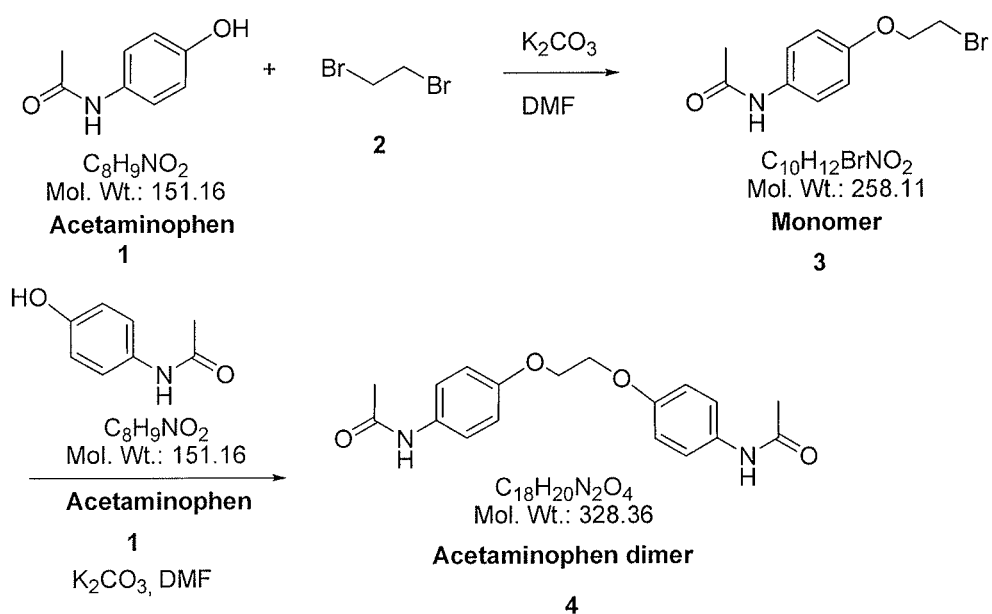
FIG. 5 provides a synthetic route to the acetaminophen dimer.

The compound was synthesized as shown in FIG. 5.
Synthesis of Intermediate 3:

Acetaminophen (1 equiv) and potassium carbonate (4 equiv) in a 3-neck round bottom flask was dissolved in anhydrous DMF (10 vol). The mixture was heated to 60° C. and 1,2-dibromoethane (4 equiv) was added. The reaction mixture was stirred at 60° C. for 16 h and TLC analysis showed consumption of acetaminophen. The mixture was diluted with MTBE, cooled to 10° C., and washed with water. The organic phase was separated, dried over magnesium sulfate, filtered and concentrated. The crude product was purified by silica gel chromatography affording pure product 3. Yield: 65%.

Synthesis of Compound 4:

Compound 3 (1 equiv), acetaminophen (1.2 equiv) and potassium carbonate (3 equiv) was dissolved in anhydrous DMF (10 vol) and the mixture was heated at 60° C. and stirred for 14 hours. TLC analysis showed consumption of intermediate 3. The mixture was diluted with MTBE and washed with water at 15-20° C. The organic phase was separated, dried over magnesium sulfate, filtered and concentrated. The crude product was purified by silica gel chromatography affording pure product 4. Yield: 78%. $^1$H NMR (300 MHz, DMSO-$d_6$): 2.14 (s, 6H, $CH_3$), 4.38 (t, 4H, $CH_2$), 6.80 (d, 4H, Ar), 7.44 (d, 4H, Ar), 9.15 (s, 2H, NH).

Example 15

Albuterol Dimer

Figure 6:
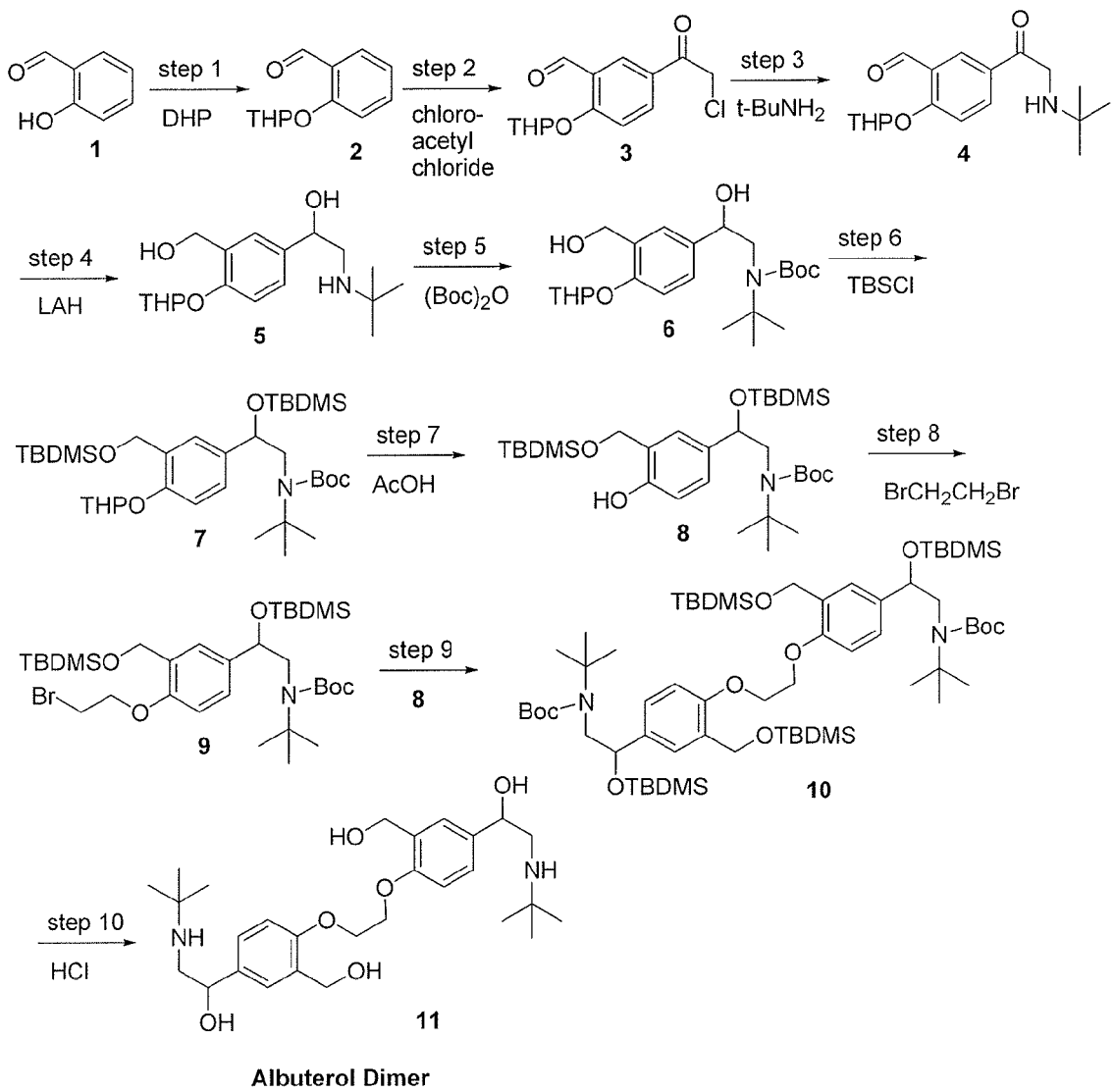
FIG. 6 provides a synthetic route to the albuterol dimer.

The compound was synthesized as shown in FIG. 6.
Synthesis of Compound 2.

Compound 1 (1 equiv) was reacted with 1.2 equiv of dihydropyran in the presence of 10 mol % PPTS in DCM at room temperature. The reaction was monitored by TLC analysis. The reaction mixture was washed with bicarbonate solution and the organic phase was dried over magnesium sulfate, filtered and concentrated. The crude product 2 was taken to the next step without further purification. Yield: 95%.

Synthesis of Compound 3.

Compound 2 (1 equiv) in DCM was treated with 1.2 equiv of aluminum chloride followed by drop-wise addition of chloroacetyl chloride (1.5 equiv) at room temperature. The reaction mixture was stirred at room temperature for 16 hours and TLC analysis indicated complete consumption of the starting material. The reaction mixture was quenched with bicarbonate solution. The organic phase was separated and dried over magnesium sulfate, filtered and concentrated. The crude product 3 was purified by silica gel chromatography to afford pure product 3. Yield: 72%.

Synthesis of Compound 4.

Compound 3 (1 equiv) was reacted with 2 equiv of butylamine in THF at room temperature. TLC analysis after 15 hours indicated complete consumption of the starting material. The reaction mixture was concentrated and the residue was purified by silica gel chromatography to afford pure product 4. Yield: 96%.

Synthesis of Compound 5.

Compound 4 (1 equiv) was dissolved in THF and cooled to 0° C. Lithium aluminum hydride (LAH) in THF (1 equiv) was added drop-wise and the mixture stirred at room temperature for 3 hours. TLC analysis shows the consumption of the starting material. Saturated aqueous sodium sulfate was added until a white precipitate formed. The solid was filtered and the filtrate concentrated under reduced pressure to afford product 5. Yield (78%).

Synthesis of Compound 6.

Compound 5 (1 equiv) in DCM was treated with 1.2 equiv of BOC-anhydride at room temperature followed by saturated sodium bicarbonate solution (2 equiv). The reaction mixture was stirred for 15 hours and TLC analysis indicated complete consumption of the starting compound. The organic phase was separated and concentrated to afford product 6. Yield (94%).

Synthesis of Compound 7.

Compound 6 (1 equiv) in DCM was treated with imidazole (1.5 equiv) followed by TBDMSCl (1.2 equiv). The reaction mixture was stirred at room temperature for 12 hours and TLC analysis indicated complete consumption of the starting compound. Water was added to the reaction mixture and the organic phase was separated, dried over magnesium sulfate, filtered and concentrated. The crude product was purified by silica gel chromatography to afford pure product 7. Yield: 85%.

Synthesis of Compound 8.

Compound 7 (1 equiv) in 7:3 acetic acid/water was heated at 60° C. for 10 hours. TLC analysis indicated complete consumption of the starting compound. The mixture was concentrated and dissolved in MTBE, and washed with bicarbonate solution. The organic phase was separated, dried over magnesium sulfate, filtered and concentrated. The crude product was purified by silica gel chromatography to afford pure product 8. Yield: 68%.

Synthesis of Compound 9.

Compound 8 (1 equiv) in DMSO was reacted with 1,2-dibromoethane (5 equiv) in the presence of anhydrous potassium carbonate (3 equiv) at 60° C. for 15 hours. TLC analysis indicated complete consumption of the starting compound. The mixture was diluted with MTBE and washed with water. The organic phase was separated, dried over magnesium sulfate, filtered and concentrated. The crude product was purified by silica gel chromatography to afford pure product 9. Yield: 62%.

Synthesis of Compound 10.

Compound 9 (1 equiv) in DMSO was reacted with compound 8 (1.2 equiv) in the presence of anhydrous potassium carbonate (2 equiv) at 50° C. for 15 hours. TLC analysis indicated complete consumption of the starting compound 9. The mixture was diluted with MTBE and washed with water. The organic phase was separated, dried over magnesium sulfate, filtered and concentrated. The crude product was purified by silica gel chromatography to afford pure product 10. Yield: 74%.

Synthesis of Compound 11.

Compound 10 (1 equiv) in MTBE was reacted with 2N HCl in ethyl acetate (10 equiv) at room temperature for 12 hours. TLC analysis indicated complete consumption of the starting compound with solid precipitation. The solid was filtered and triturated with ethyl acetate to afford product 11. Yield: 88%.

$^1$H NMR (300 MHz, DMSO-$d_6$): 1.04 (s, 18H, CH$_3$), 2.57 (d, 4H, CH$_2$), 4.42 (t, 2H, CH), 4.45 (t, 4H, CH$_2$), 4.49 (s, 4H, CH$_2$), 4.63 (s, 6H, OH and NH), 6.71 (d, 2H, Ar), 7.01 (d, 2H, Ar), 7.29 (s, 2H, Ar).

Example 16

Illustrative Pharmaceutical Compositions

The pharmaceutical composition in Table 2 can be used for oral tablets of the dimers of the invention.

TABLE 2

| Ingredients | % w/w |
|---|---|
| Dimer | 2 |
| Lactose | 83.6 |
| Colloidal Silicon dioxide | 0.67 |
| Microcrystalline cellulose | 10 |
| Croscarmellose sodium | 3.4 |
| Magnesium stearate | 0.33 |

Example 17

Illustrative Doses

The dose of the dimers provided herein to be administered to a patient is rather widely variable and can be subject to the judgment of a health-care practitioner. Dosage may be properly varied depending on the age, body weight and medical condition of the subject and the type of administration. In one embodiment, one dose is given per day. In any given case, the amount of the dimer provided herein administered will depend on such factors as the solubility of the active component, the formulation used and the route of administration. By "therapeutically effective dose" we mean a dose that yields an appreciable and beneficial effect in a statistically significant number of patients. In certain embodiments, the patient is a mammal. In more specific embodiments, the patient is a human. In certain specific embodiments, the patient may be a domesticated mammal such as a dog, a cat, or a horse.

Preferred dosages for IBS-D Patients, for example, are about 0.15 mg/kg of an IBS-D patient's body weight to about 7.2 mg/kg of a patient's body weight, more preferably from about 0.7 mg/kg of an IBS-D patient's body weight to about 3.0 mg/kg of a patient's body weight, and still more preferably about 1.5 mg/kg of a patient's body weight in unit dosage for oral administration. Alternatively, from about 10 to about 500 mg, preferably from about 50 to about 200 mg, more preferably about 100 mg, will be administered to an IBS-D patient. In Table 3 we provide putative dosages of dimers according to the invention for preferred indications, compared to those of the monomers for their own indications. The transformative effect of dimerization in extending the reach of these active agents will be apparent from the Table.

TABLE 3

| Monomer | Indication | Dose | | Dimer Indication | Dimer dose | |
|---|---|---|---|---|---|---|
| Buprenorphine | Opioid addiction | 2-32 | mg/SL | IBS-D | 50-200 | mg PO |
| Naloxone | Opioid abuse | 0.5-2 | mg IV/SC | Opioid-induced constipation | 100-200 | mg PO |
| Naltrexone | Opioid abuse | 50 | mg PO | Opioid-induced constipation | 100-200 | mg PO |
| Desvenlafaxine | Anti-depressant | 50 | mg PO | Gastroparesis, constipation, ileus | 50-200 | mg PO |
| Albuterol | Bronchospasm | 50 | mg IN | Bronchospasm | 5-10 | mg PO |
| Acetaminophen | Analgesia | 500 | mgs PO | Liver-safe analgesia | 500-1000 | mg PO |

It is understood that the examples and embodiments described herein are for illustrative purposes only and that various modifications or changes in light thereof will be suggested to persons skilled in the art and are to be included within the spirit and purview of this application and scope of the appended claims. To the extent there is conflict between the priority applications and the present application, any inconsistencies are to be resolved in favor of the present application. All publications and patents cited herein are hereby incorporated by reference in their entirety for all purposes.

What is claimed is:

1. A homo-dimer compound of a pharmaceutically active agent selected from the group consisting of naloxone, naltrexone, des-venlafaxine and albuterol wherein two such agents are covalently ether-linked through phenolic hydroxyl groups of the agents by an ethylene residue, or a pharmaceutically acceptable salt or solvate thereof.

2. A homo-dimer compound according to claim 1, wherein the compound is in the form of a pharmaceutically acceptable salt.

3. A pharmaceutical composition comprising a pharmaceutically acceptable carrier or excipient and a dimer compound according to claim 1 or 2.

4. The pharmaceutical composition of claim 3, wherein said composition is formulated as an oral tablet or capsule or extended release oral tablet or capsule.

5. A naloxone dimer compound having the Formula:

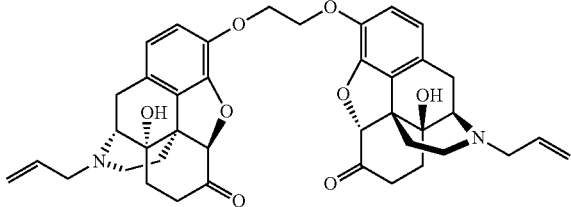

or a pharmaceutically acceptable salt or solvate thereof.

6. A naltrexone dimer compound having the Formula:

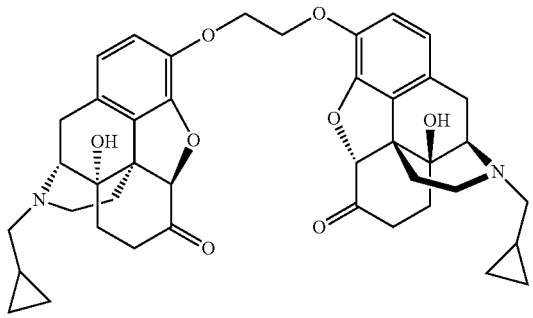

or a pharmaceutically acceptable salt or solvate thereof.

7. A des-venlafaxine dimer compound having the Formula:

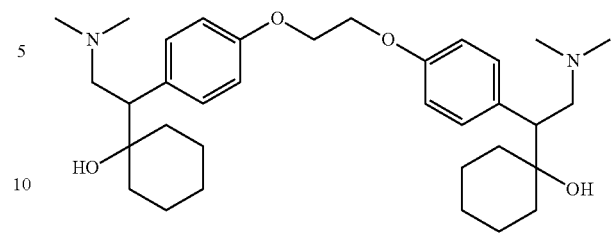

or a pharmaceutically acceptable salt or solvate thereof.

8. An albuterol dimer compound having the Formula:

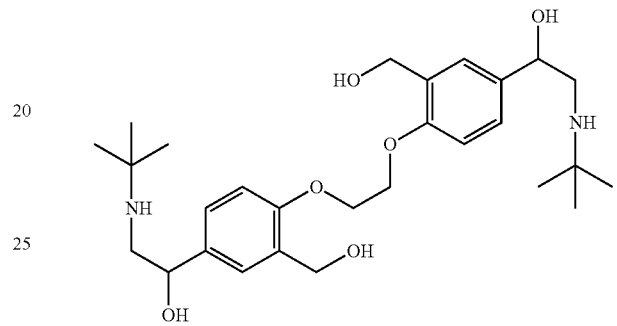

or a pharmaceutically acceptable salt or solvate thereof.

9. A homo-dimer compound of claim 2, wherein the pharmaceutically acceptable salt is a citric acid salt.

10. A dimer compound of any one of claim 5, 6 7 or 8, in a citric acid salt form.

* * * * *